(12) United States Patent
Adair et al.

(10) Patent No.: US 8,071,132 B2
(45) Date of Patent: *Dec. 6, 2011

(54) UNAGGLOMERATED CORE/SHELL NANOCOMPOSITE PARTICLES

(75) Inventors: James H. Adair, University Park, PA (US); Sarah M. Rouse, University Park, PA (US); Jun Wang, Northboro, MA (US); Mark Kester, Hershey, PA (US); Christopher Siedlecki, Hershey, PA (US); William B. White, University Park, PA (US); Erwin Vogler, University Park, PA (US); Alan Snyder, Hershey, PA (US); Carlo G. Pantano, University Park, PA (US); Victor Ruiz-Velasco, Hershey, PA (US); Lawrence Sinoway, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 1231 days.

This patent is subject to a terminal disclaimer.

(21) Appl. No.: 11/142,913

(22) Filed: Jun. 1, 2005

(65) Prior Publication Data

US 2005/0281884 A1    Dec. 22, 2005

Related U.S. Application Data

(60) Provisional application No. 60/575,887, filed on Jun. 1, 2004, provisional application No. 60/579,214, filed on Jun. 14, 2004.

(51) Int. Cl.
*A61K 9/14* (2006.01)
(52) U.S. Cl. ............ 424/489; 424/450; 435/6; 436/525; 436/527; 428/402; 428/402.2; 428/402.24; 428/403; 428/405
(58) Field of Classification Search .................. None
See application file for complete search history.

(56) References Cited

U.S. PATENT DOCUMENTS

| | | | |
|---|---|---|---|
| 6,413,489 B1 | 7/2002 | Ying et al. | |
| 6,548,264 B1 | 4/2003 | Tan et al. | |
| 6,555,376 B2 | 4/2003 | Maitra et al. | |
| 6,558,658 B2 | 5/2003 | Harris | |
| 6,627,314 B2 | 9/2003 | Matyjaszewski et al. | |
| 6,869,584 B2 | 3/2005 | Ying et al. | |
| 6,924,116 B2 | 8/2005 | Tan et al. | |
| 7,018,657 B2 | 3/2006 | Dickinson et al. | |
| 2003/0206859 A1 | 11/2003 | Chen et al. | |
| 2004/0067503 A1 | 4/2004 | Tan et al. | |
| 2004/0115239 A1 | 6/2004 | Shastri et al. | |
| 2005/0025820 A1* | 2/2005 | Kester et al. ............ | 424/450 |
| 2005/0152832 A1 | 7/2005 | Ying et al. | |
| 2005/0281884 A1 | 12/2005 | Adair et al. | |
| 2006/0093557 A1 | 5/2006 | Dickinson et al. | |

FOREIGN PATENT DOCUMENTS

| | | |
|---|---|---|
| DE | 10164768 A1 | 10/2003 |
| JP | 04-114730 | 4/1992 |
| WO | WO 01/62232 A1 | 8/2001 |
| WO | WO 01/88540 A1 | 11/2001 |

OTHER PUBLICATIONS

Bae et al., Synthesis of Cu/SiO2 Nanosize Particles by a Reverse Micelle and Sol-Gel Processing; Journal of Materials Science Letters; 2002; pp. 53-54; vol. 21.
Ying et al., One-Step Synthesis of Water-Soluble Gold Nanoparticles/polyaniline Composite and its Application in Glucose Sensing; Colloids and Surfaces A: Physicochem. Eng. Aspects; 2005; pp. 1-6; vol. 269.
Liz-Marzan et al., "Synthesis of Nanosized Gold-Silica Core-Shell Particles," Langmuir, 1996, 12, 4329-4335.
Adair et al., "Particle-Size Analysis of Ceramic Powders," Advances in Ceramic, The American Ceramic Society, 1984, vol. 11, OH, 142-156.
Arriagada et al., "Controlled hydrolysis of tetraethoxysilane in a nonionic water-in-oil microemulsion: a statistical model of silica nucleation," Colloids and Surfaces A: Physicochemical and Engineering Aspects 154, 1999, 311-326.
Arriagada et al., "Growth Kinetics of Nanosize Silica in a Nonionic Water-in-Oil Microemulsion: A Reverse Micellar Pseudophase Reaction Model," Journal of Colloid and Interface Science, 218, 1999, 68-76.
Arriagada et al., "Synthesis of Nanosize Silica in a Nonionic Water-in-Oil Microemulsion: Effects of the Water/Surfactant Molar Ratio and Ammonia Concentration," Journal of Colloid and Interface Science, 211, 1999, 210-220.
Bisht et al., "pDNA loaded calcium phosphate nanoparticles: highly efficient non-viral vector for gene delivery," International Journal of Pharmaceutics, 288, 2005, 157-168.
Chiang et al., "Magic-Angle Cross-Polarization Carbon 13 NMR Study of Aminosilane Coupling Agents on Silica Surfaces," Journal of Colloid and Interface Science, 1982, 86(1): 26-34.
Chiang et al., "The Structure of (-Aminopropyltriethoxysilane on Glass Surfaces," Journal of Colloid and Interface Science, 1980, 74(2): 396-403.

(Continued)

*Primary Examiner* — Susan Tran
*Assistant Examiner* — Hasan Ahmed
(74) *Attorney, Agent, or Firm* — McKee, Voorhees & Sease, P.L.C.

(57) ABSTRACT

The present invention provides a method for the synthesis of unagglomerated, highly dispersed, stable core/shell nanocomposite particles comprised of preparing a reverse micelle microemulsion that contains nanocomposite particles, treating the microemulsion with a silane coupling agent, breaking the microemulsion to form a suspension of the nanocomposite particles by adding an acid/alcohol solution to the microemulsion that maintains the suspension of nanocomposite particles at a pH of between about 6 and 7, and simultaneously washing and dispersing the suspension of nanocomposite particles, preferably with a size exclusion HPLC system modified to ensure unagglomeration of the nanocomposite particles. The primary particle size of the nanocomposite particles can range in diameter from between about 1 to 100 nm, preferably from between about 10 to 50 nm, more preferably about 10 to 20 nm, and most preferably about 20 nm.

42 Claims, 28 Drawing Sheets

OTHER PUBLICATIONS

Hackley and Ferraris, "The use of nomenclature in dispersion science and technology," Special Publ. 960-3, National Institute of Standards and Technology, U.S. Department of Commerce, pp. 7-8, Aug. 2001, Superintendent of Documents, U.S. Government Printing Office, Mail Stop SSOP, Washington, DC, 20402-0001.

Haugland, R.P., Molecular Probe, 6:320-328, 1998.

Li et al., "Preparation of Ag/SiO$_2$ Nanosize Composites by a Reverse Micelle and Sol-Gel Technique," Langmuir, 1999, 15(13), 4328-4334.

Maulvaney et al., "Synthesis of Nanosized Gold-Silica Core-Shell Particles," Langmuir, 1996, 12, 4329-4335.

Plueddemann, Chemistry of Silane Coupling Agents, Silane Coupling Agents, Chapter 2, Plenum Press, NY, 1982, 29-48.

Roy et al., "Calcium phosphate nanoparticles as novel non-viral vectors for targeted gene delivery," International Journal of Pharmaceutics, 250, 2003, 25-33.

Ung et al., "Controlled Method for Silica Coating of Silver Colloids. Influence of Coating on the Rate of Chemical Reactions," Langmuir, 1998, 14(14), 3740-3748.

Zhao et al., "Development of Organic-Dye-Doped Silica Nanoparticles in a Reverse Microemulsion," Advanced Materials, 2004, 16(2), 173-176.

Zhan Huan Zhou et al. *Biologically Inspired Nanotechnology*.

P. Srinath et al., *Stealth Liposomes—An Overview*, Indian Journal of Pharmacology, 1994, vol. 26, 179-184.

Andreas Zimmer et al., *Microspheres and nanoparticles used in ocular delivery systems*, Advanced Drug Delivery Reviews, 1995, vol. 16, 61-73.

Weojpmg Tam et al, *Neurotransmitter Imaging in Living Cells Based on Native Fluorescence Detection*, Analytical Chemistry, vol. 67, No. 15, Aug. 1, 1995, 2575-2579.

Gert Storm et al., *Surface Modification of Nanoparticles to Oppose Uptake by the Mononuclear Phagocyte System*, Advanced Drug Delivery Reviews, vol. 17, 1995, 31-48.

Vinod Labhasetwar et al., *Nanoparticle Drug Delivery System for Restenosis*, Advanced Drug Delivery Reviews, vol. 24, 1997, 63-85.

Nicholas Leventis et al., American Chemical Society, vol. 9, 1997, 2621-2631.

J.H. Adair et al., *Recent Developments in the Preparation and Properties of Nanometer-Size Spherical and Platelet-Shaped Particles and Composite Particles*, Materials Science and Engineering, R23, 1998, 139-242.

Tapan Kumar Jain et al., *Nanometer Silica Particles Encapsulating Active Compounds: A Novel Ceramic Drug Carrier*, American Chemical Society, vol. 120, 1998, 11092-11095.

Tuo Li et al., *Preparation of Ag/SiO$_2$ Nanosize Composites by a Reverse Micelle and Sol-Gel Technique*, Langmuir The ACS Journal of Surfaces and Colloids, vol. 15, No. 13, 4328-4334, 1999.

Sotiris E. Kakabakos et al., *Heterogeneous Fluoroimmunoassays Using Fluorescein as Label with Measurement of the Fluorescence Signal Directly Onto the Solid-Phase*, Journal of Immunological Methods vol. 222, 1999, 183-187.

Harri Harma et al., *Immunoassay on a Single Microparticle: The Effect of Particle Size and Number on a Miniaturized Time-Resolved Fluorometric Assay of Free Prostate-Specific Antigen*, Analytica Chimica Acta, vol. 387, 1999, 11-19.

James H. Adair et al., *Morphological Control of Particles*, Current Opinion in Colloid & Interface Science, vol. 5, 2000, 160-167.

Marta Alejandro-Arellano et al., *Silica-Coated Metals and Semiconductors. Stabilization and Nanostructuring*, Pure Appl. Chem., vol. 72, Nos. 1-2, 2000, 257-267.

Makoto Ogawa, et al., *Luminescence of Tris(2,2'-bipyridine)ruthenium(II) Cations ($[Ru(bpy)_3]^2$) Adsorbed in Mesoporous Silica*, American Chemical Society, vol. 104, 2000, 8554-8556.

Swadeshmukul Santra et al., *Conjugation of Biomolecules with Luminophore-Doped Silica Nanoparticles for Photostable Biomarkers*, Analytical Chemistry, vol. 73, No. 20, Oct. 15, 2001, 4988-4993.

Jorg Kreuter, *Nanoparticulate Systems for Brain Delivery of Drugs*, Advanced Drug Delivery Reviews, vol. 47, 2001, 65-81.

W. Yang et al., *Novel Fluorescent Silica Nanoparticle Probe for Ultrasensitive Immunoassays*, Analytica Chimica Acta, vol. 503, 2004, 163-169.

Dr. Ralf Norenberg, *Sinking One's Teeth into Nanotechnology: Hydroxyapatite and Tooth Repair*, Journalists and Scientists in Dialogue Nanotechnology in Chemistry—Experience meets Vision Conference on Oct. 18-29, 2002 in Mannheim.

Hua Jane Lou et al., *Molecular Beacons Offer a Highly Sensitive, Flexible Method for DNA Analysis*, Spie's oe Magazine, Feb. 23-25, 2002.

Dhruba Jyoti Bharali et al., *Cross-linked polyvinylpyrrolidone nanoparticles: A Potential Carrier for Hydrophilic Drugs*, Journal of Colloid and Interface Science, vol. 258, 2003, 415-423.

A. Barroug et al., *Interactions of Cisplatin with Calcium Phosphate Nanoparticles: In Vitro Controlled Adsorption and Release*, Journal of Orthopaedic Research, xxx (2003) xxx-xxx.

Huang-Hao Yang et al., *Nanometer Fluorescent Hybrid Silica Particle as Ultrasensitive and Photostable Biological Labels*, The Royal Society of Chemistry, 2003.

L. Mu et al., *A Novel Controlled Release Formulation for the Anticancer Drug Paclitaxel (Taxol®): PLGA Nanoparticles Containing Vitamin E TPGS*, Journal of Controlled Release, vol. 86, 2003, 33-48.

Laura Mazzola, *Commercializing Nanotechnology*, Focus on Nanobiotechnology, vol. 21, 2003, 1137-1143.

Jian-Feng Chen et al., *Preparation and Characterization of Porous Hollow Silica Nanoparticles for Drug Delivery Application*, Biomaterials, vol. 25, 2004, 723-727.

Zs. Csogor et al., *Modified Silica Particles for Gene Delivery*, Materials Science and Engineering, vol. C 23, 2003, 93-97.

Tao Lu Lowe, *Thermo-Responsive and Biodegradable Polymeric Systems for Drug Delivery and Tissue Engineering*, Journal Club, 2003.

Li et al., "Preparation of Ag/Si02 Nanosize Composites by a Reverse Micelle and Sol-Gel Technique," Langmuir, 1999, 15(13), 4328-4334.

* cited by examiner

SCHEMATIC OF THE REVERSE-MICELLE SYNTHESIS, WASHING AND COLLECTION APPROACH.

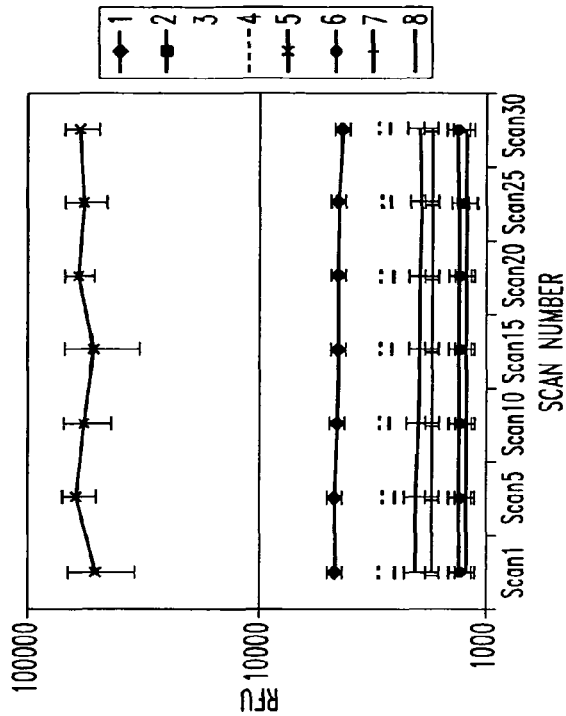
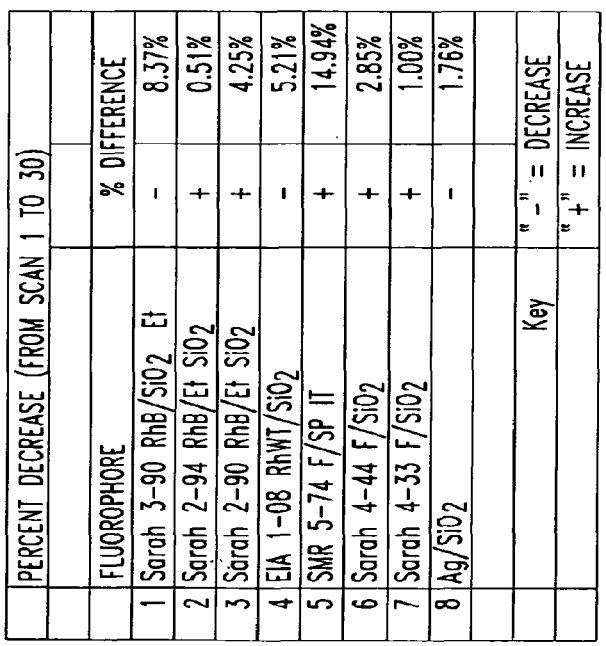
FIG. 5
NANOCOMPOSITE PARTICLE PHOTODECAY EXPERIMENT RESULTS (NOTE NEGLIGIBLE DECAY AFTER 30 SCANS UNDER INTENSE LASER LIGHT). (DATA COURTESY OF S. CONZONE, SCHOTT NEXTERION AG, DUEYEA, PA).

Fig. 6A-D

Fig. 7A-E 1 reservoir, 2 pump, 3 column, 4 UV-vis detector,
5 fraction collector

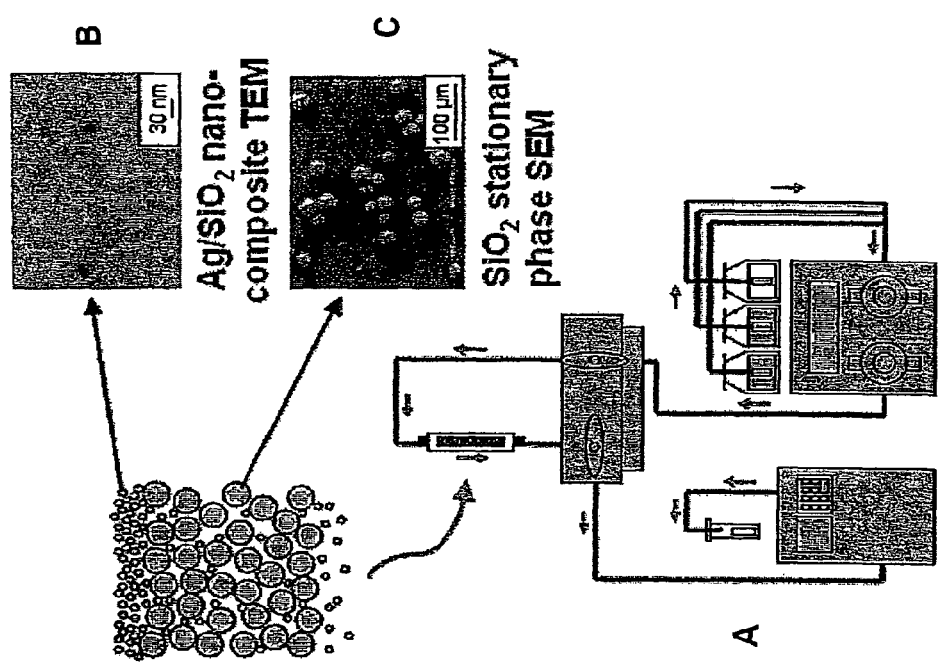
Fig. 12A-C

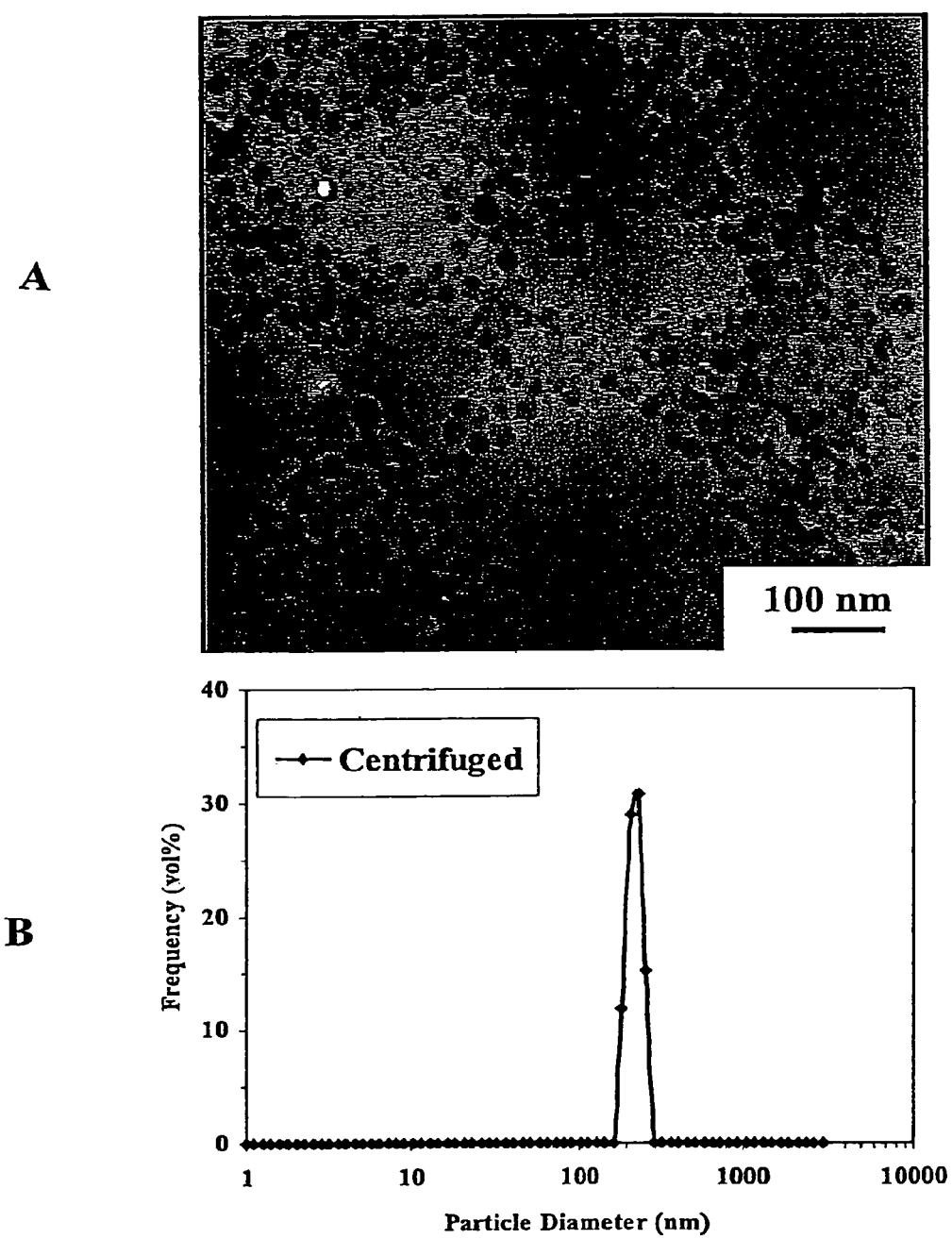
Fig. 13A-B

A 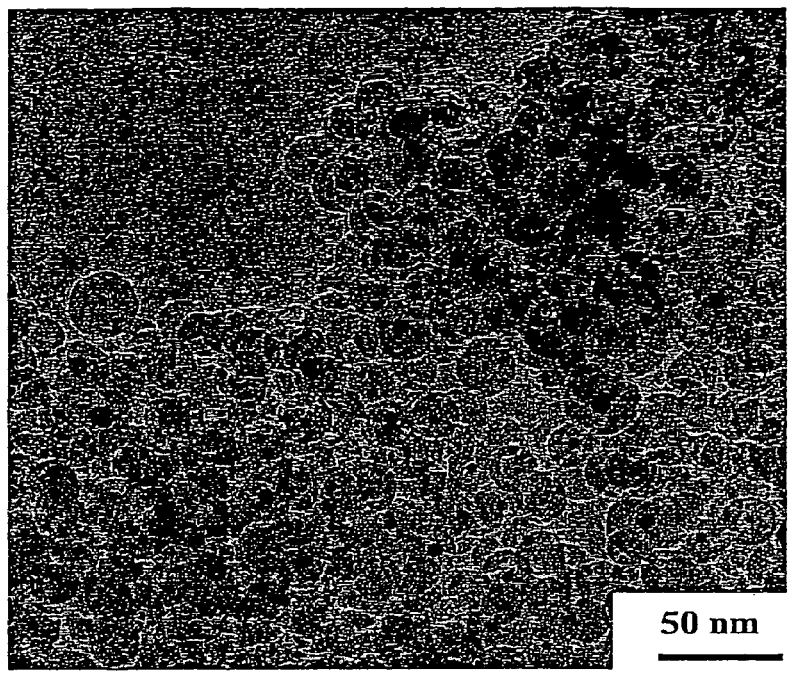
B 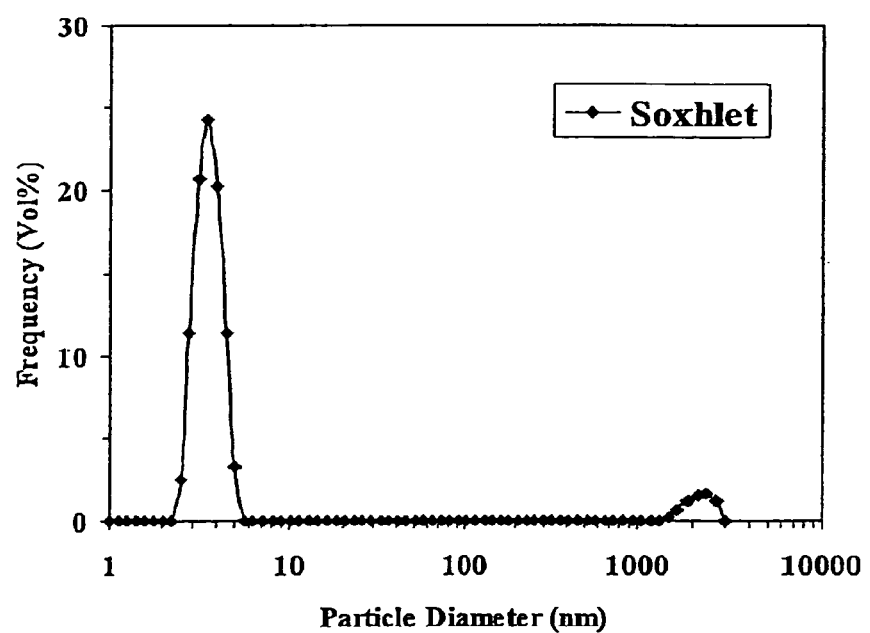
Fig. 14A-B

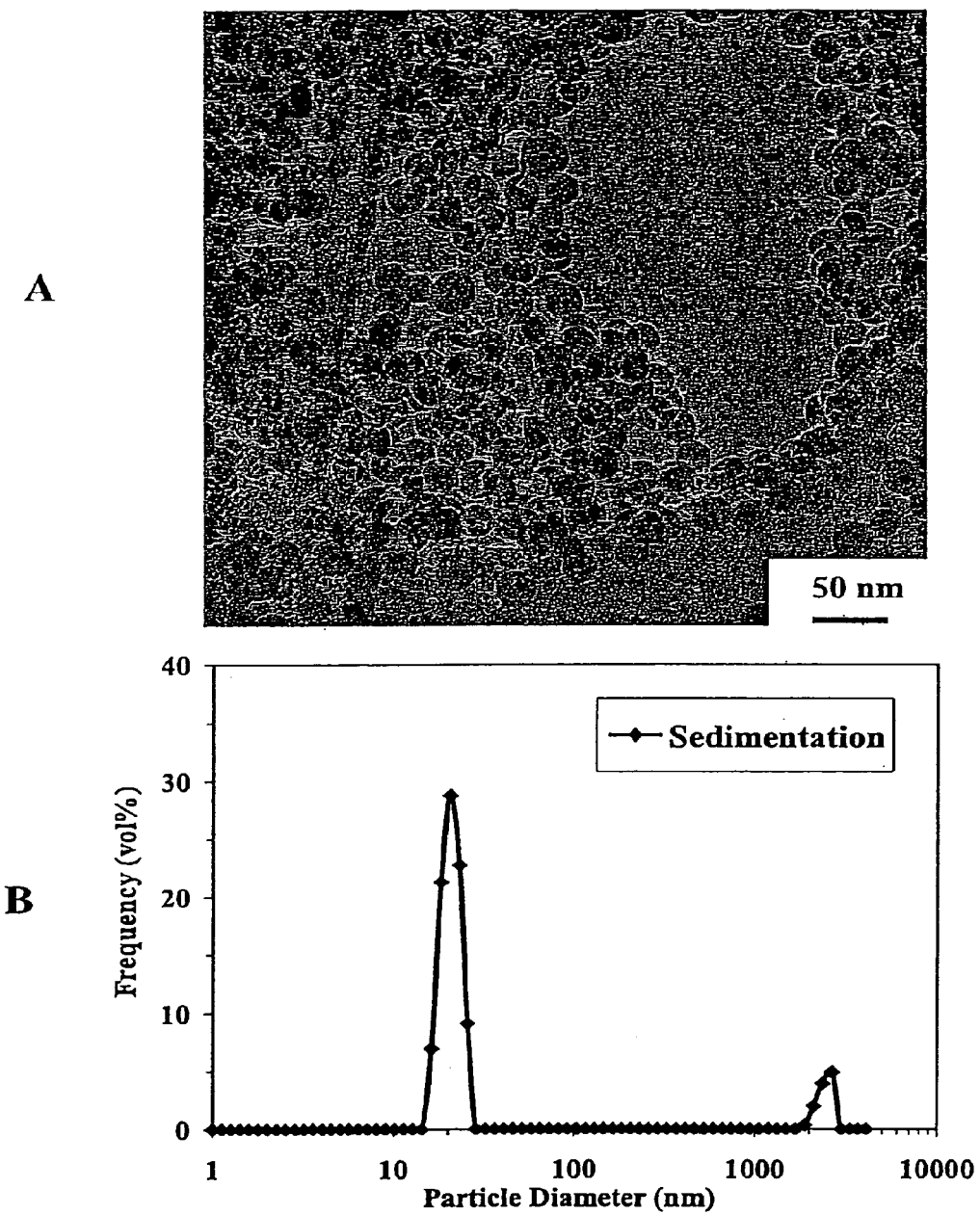
Fig. 15A-B

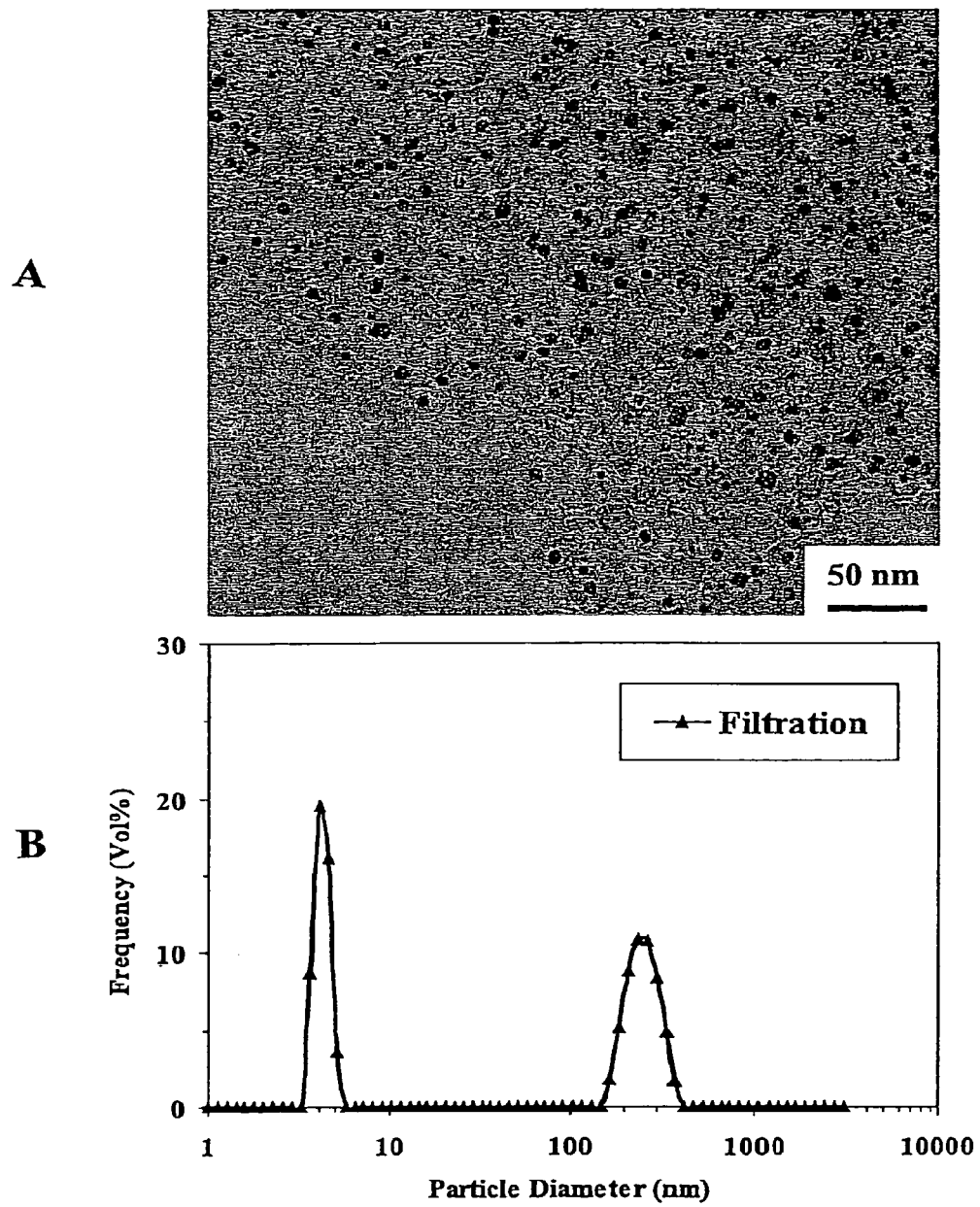
Fig. 16A-B

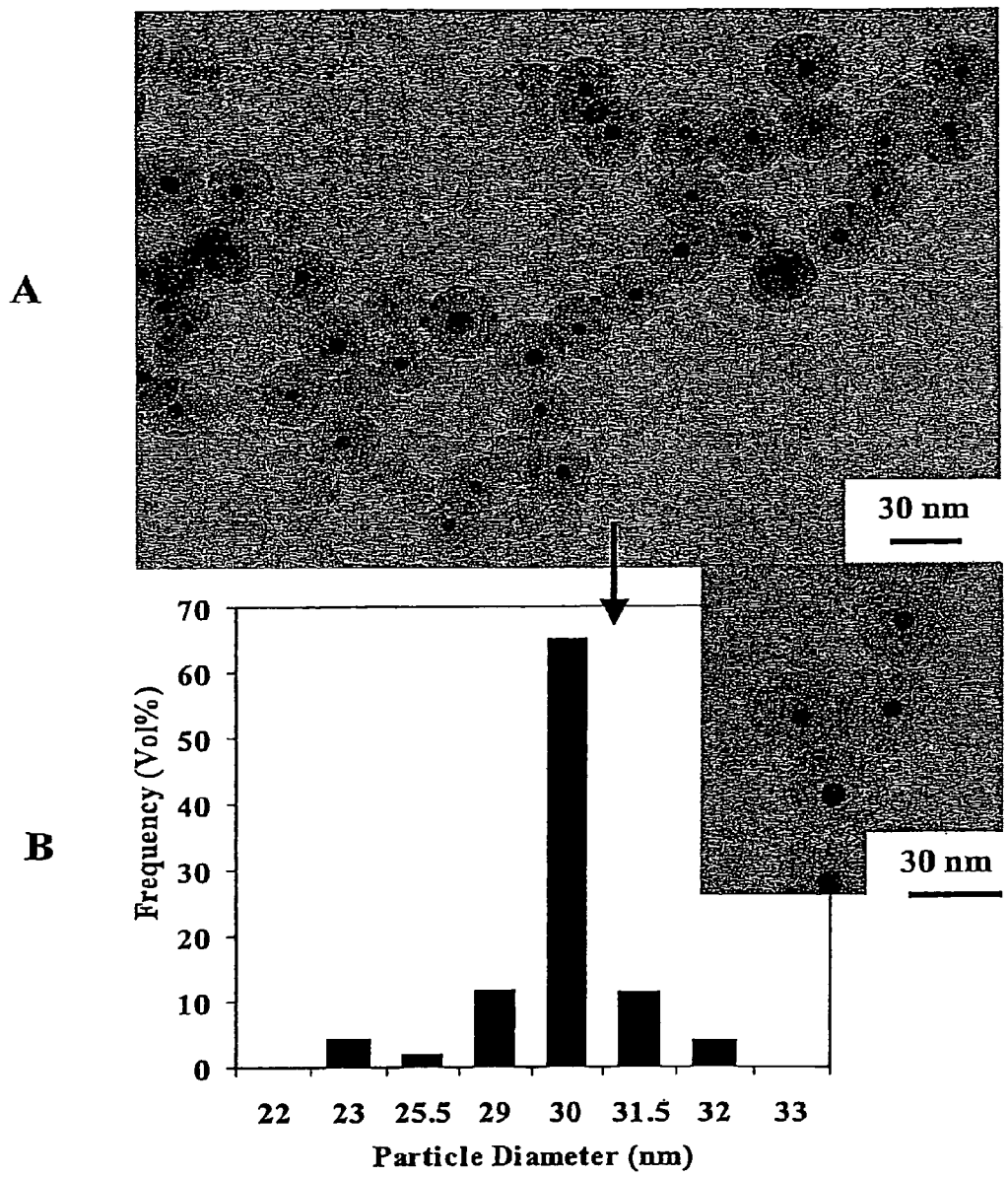
Fig. 17A-B

Fig. 20A-B

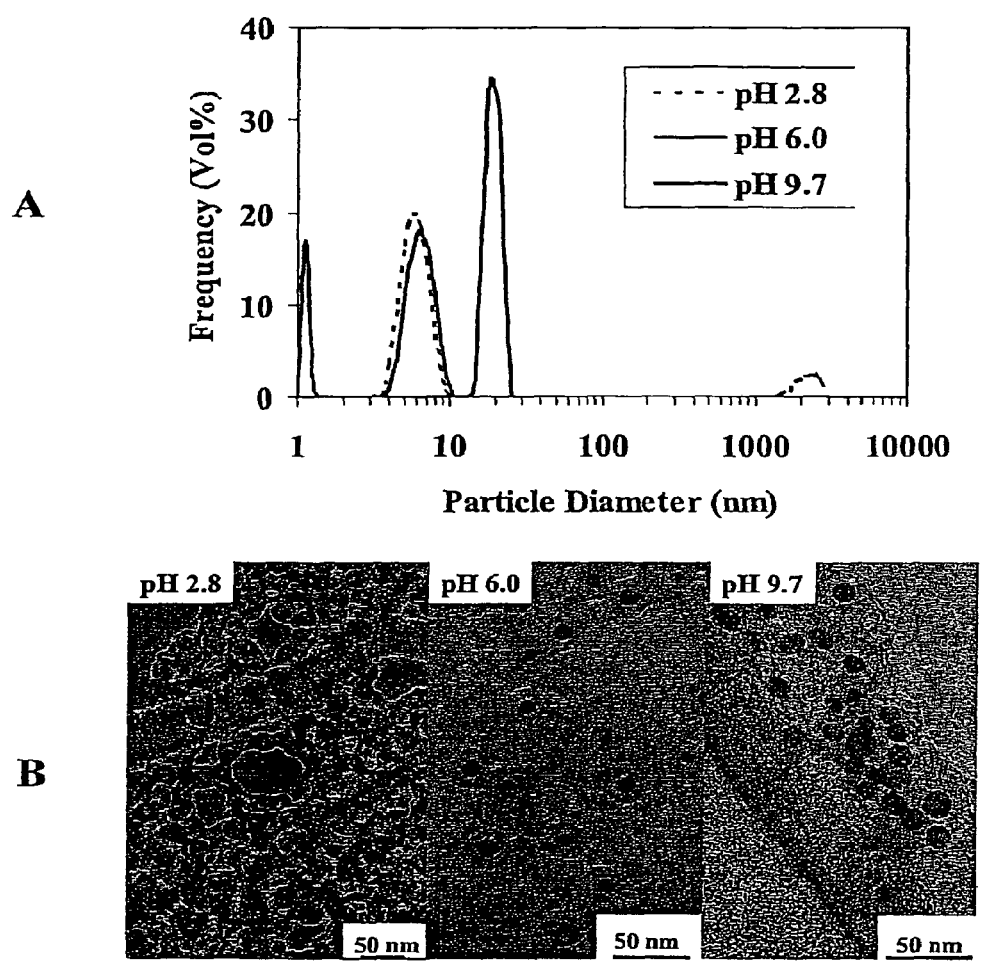
Fig. 26A-B

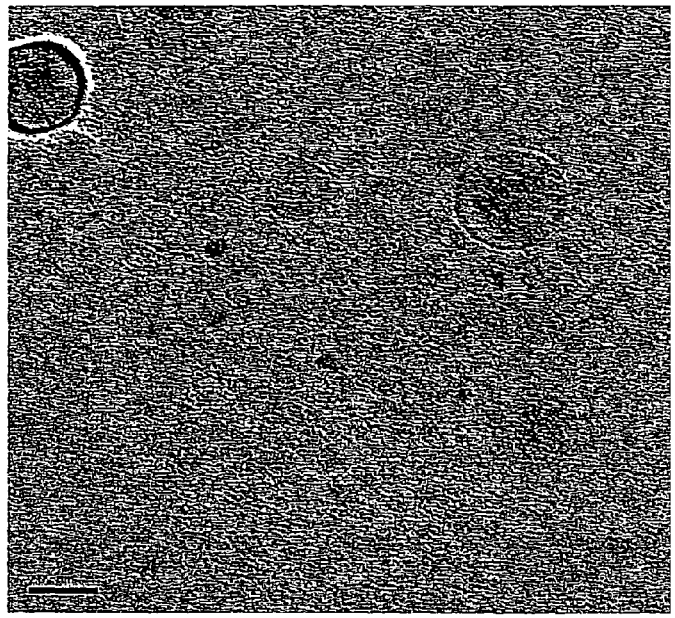
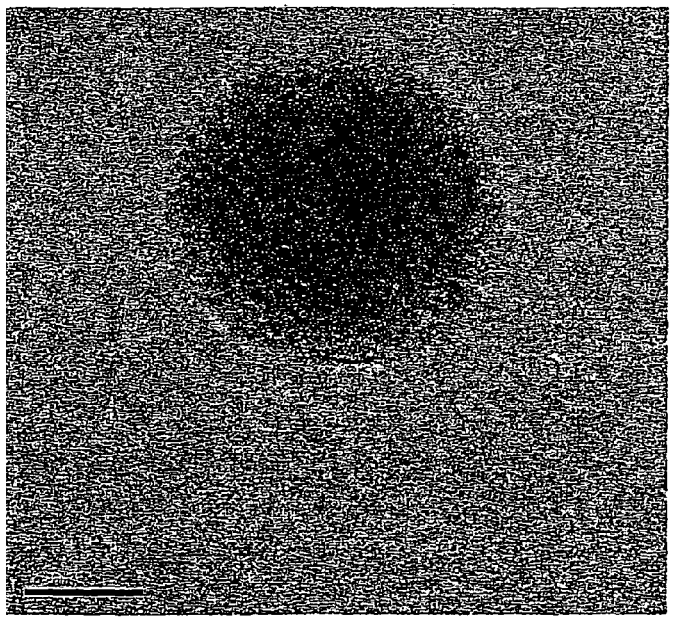
Fig. 27A-B

Table 1 Silane coupling agents for surface modification of $SiO_2$ based particles

| Name | Structure | pH window | Remarks | References |
|---|---|---|---|---|
| 3-aminopropyl-trimethoxysilane (APS) | $H_2NC_3H_6Si$-$(OCH_3)_3$ (or $OC_2H_5$) | 2.0–9.0 | Modify the surface of $SiO_2$ | Plueddemann [1] Mulvaney [2] Mann [3] |
| 3-aminopropyl-silsesquioxane | $(H_2N)_8(CH_2)_{24}$-$O_{12}Si_8$ | 2.0 ~ 6.5 | Surface coating of $SiO_2$ and Ag | Caruso [4] |
| 3-glycidoxypropyl-trimethoxysilane (GPS) | $H_2NC_6H_{11}O_2$-$Si(OCH_3)_3$ | < 9.0 | Modify $SiO_2$ surfaces | Schmidt [5] |
| Trimmethoxysilylpropyldiethylenetriamine (DETA) | $(H_2N)_3C_7H_{12}$-$Si(OCH_3)_3$ | 6.8 | Surface coating of $SiO_2$ | Tan [6] |
| 3-trimethoxysilypropylsuccinic anhydride | $C_8H_{11}O_3$-$Si(OCH_3)_3$ | > 8.0 | Surfaces coating of $SiO_2$ | Hemplemann [7] |

[1] E. P. Plueddemann, Silane Coupling Agents, Plenum Press, New York, 1982.

[2] T. Ung, L. M. Liz-Marzan and Paul Mulvaney, Langmuir, 14, 3740-3748, (1998).

[3] S. R. Hall S. A. Davis and S. Mann, Langmuir, 16, 1454-1456, (2000).

[4] T. Cassagneau and F. Caruso, Adv. Mater., 14, 732-736, (2002).

[5] Z. Csogor, M. Nacken, M. Sameti, C.M. Lehr and H. Schmidt, Mater. Sci. Eng. C., 23, 93-97, (2003).

[6] S. Santra, P. Zhang, K. Wang, R. Tapec and W. Tan, Anal. Chem., 73, 4988-4993, (2001).

[7] C. Beck, W. Hartl and R. Hemplemann, Angew. Chem. Int. Ed., 38, 1297-1300, (1999).

Fig. 28

UNAGGLOMERATED CORE/SHELL NANOCOMPOSITE PARTICLES

The present application claims priority to U.S. Provisional Application No. 60/575,887, filed Jun. 1, 2004, and to U.S. Provisional Application No. 60/579,214, filed Jun. 14, 2004, both of which are incorporated herein by reference.

BACKGROUND OF THE INVENTION

1. Field of the Invention

The present invention relates to nanocomposite particles. More particularly, the present invention provides a method for synthesizing stable, well dispersed, unagglomerated core/shell nanocomposite particles of varying sizes that may be used for a wide variety of applications.

2. Description of Related Art

One of the most important developments in the field of chemical technologies is that of nanostructuring. Nanostructured materials are assemblies of nano-sized units that display unique, characteristic properties at a macroscopic scale. The size range of such units lies within the colloidal range, where the individual properties are different to both those of atoms/molecules and to those of the bulk. The properties of the nanostructured assemblies, therefore, can be tuned by varying the colloidal properties of the constituents, mainly particle size, surface properties, interparticle interactions and interparticle distance.

The use of nanoparticles in biomedical applications is a major focus of numerous research groups today. Nanoparticles possess several qualities that make them useful in biomedical applications, such as diagnostic bioimaging, drug delivery, and gene therapy. Nanoparticles also can be used as bioimaging agents to label cells in cultures, tissues, or intact organisms.

Current nanoparticle technologies used in bioimaging applications include magnetic nanoparticles, ferrofluids, and quantum dots (QDs). Recently, there have been numerous advances in the development of colloidal fluorescent semiconductor nanocrystals, a class of QDs used for biological labeling (marketed as Q-dots™), such as ZnS shell-CdSe core nanoparticles. (Haugland, R. P. Molecular Probe, 6:320-328, 1998). Researchers are in the process of developing bioconjugation schemes and applying such probes to biological assays, and nanocrystals can be of particular benefit as biological labels when compared to existing organic dyes. Quantum dots have been widely tested in a range of bioimaging applications.

Semiconductor nanocrystals have several problems associated with their use, such as solubility, physicochemical stability and quantum efficiency of the semiconductor nanocrystals. Additionally, QD emissions are strongly intermittent and agglomeration can limit their effectiveness as a bioimaging tool. Other problems associated with QDs include surface electronic defects and toxicological effects, as surface oxidation can cause degradation of the QD shell, releasing toxic metals into the body, and poor crystallinity, which makes the interpretation of the physical properties of QDs very difficult. Furthermore, the routine application of fluorescent nanoparticles as biolabels is controversial, particularly because of general environmental concerns regarding the use of highly toxic compounds, such as cadmium, in biomedical diagnostics. Moreover, methods for designing nanometer-sized structures and controlling their shape to yield new materials with novel electronic, optical, magnetic, transport, photochemical, electrochemical and mechanical properties are rarely found and present a potentially rewarding challenge.

Nanoparticles also can function as a mechanism for drug delivery, which permits the utilization of numerous water-insoluble and unstable drugs. Additionally, nanoparticles can find use in drug targeting and extended release applications based on resorbable shell technologies. In addition, nanocomposites can be used in gene therapy for the delivery of genetic materials. Current nanoparticle drug and gene "carriers" include polymeric micelles, liposomes, low-density lipoproteins, polymeric nanospheres, dendrimers, and hydrophilic drug-polymer complexes.

Over the past ten years, extensive research has been carried out in the field of fabrication of nanoscale composite particles because of their unique properties and potential applications in electronics and photonics. Silicon dioxide ($SiO_2$)-shell metallic-core structured nanocomposite particles were first synthesized and reported by Mulvaney et al. (Langmuir, 12:4329-4335, 1996), and by Adair et al. (Materials Sci. & Eng. R., 23:139-242, 1998). Most of the $SiO_2$ coated nanocomposite particles having a core-shell architecture fall into two categories based on the synthetic method used. The approach developed by Mulvaney et al. involved the modification of metal cluster surfaces with the silane-coupling agent 3-aminopropyltriethoxysilane (APS) before the formation of the silica shell. APS is used as an adhesion promoter between the vitreophobic metal cluster core and the $SiO_2$. The state of dispersion for the nanocomposites in suspension, however, was not examined by Mulvaney et al. or Adair et al. Adair et al. were successful in coating metallic and CdS clusters with $SiO_2$ via simple hydrolysis and condensation of tetrethoxysilane (TEOS) in a cyclohexane/Igepal/water tertiary system having an aqueous phase. This system allows for a very uniform silica-shell coating along with a tunable thickness of both the core and the shell due to the confining of water droplets in oil.

Major limitations in the use of nanoparticles in therapeutic agent delivery applications involve the lack of colloidal stability in nanoparticle suspensions, agglomeration, polydispersity in size and shape, swelling, and leakage. Other problems include difficulty of synthesis and processing techniques, inadequate loading inside the carrier particle, and lack of applicability to a variety of medical agents. Residual precursor materials present in unwashed nanosuspensions can also have detrimental effects for both targeted delivery and toxic effects on the physiological system. In a typical chemical synthetic method, dispersion of nanoparticles essentially begins with the washing of the freshly prepared nanoparticles. However, washing and dispersion of nanoparticles is a challenge because of the strong van der Waals attraction between adjacent nanoparticles. For this reason, nanoparticle suspensions usually are stabilized with surface coatings of surfactant, which effectively balances the interaction forces with a high repulsion potential created by the surfactant molecules. It is necessary, however, to minimize the surfactant dispersants in order to achieve better performance for nanoparticle-based applications and devices. This is because surfactant additives are transferred to the subsequent process steps and can negatively impact the homogeneity of the arrays assembled from the nanoparticles. Furthermore, when protective surfactants are removed with conventional washing techniques, such as centrifugation, the nanoparticles tend to undergo agglomeration. The presence of agglomerates also can compromise the effective yield of particles. If nanometer-size primary particles are desired, the presence of agglomerates that are generally an order of magnitude or larger in size must be avoided. For example, prior art conventional methods for fabricating nanocomposite particles, such as filtration methods, as disclosed in U.S. Pat. No.

6,548,264, 2003 to Tan, W. et al., and discussed in more detail below, result in nanocomposite particles that are irreversibly agglomerated with an agglomeration size of about 250 nm.

Considering the current limitations in nanomedicine, there is a need for a universally applicable nanoparticle with controlled time-release, high loading of therapeutic agent(s), ease of preparation, stability, and up-scaling capabilities. The formulation of a stable, non-aggregating colloid to deliver active-medical-agents has the potential to transform the medical field by providing universal, controlled, targeted, systemic delivery for a variety of bioimaging and therapeutic agents.

SUMMARY OF THE INVENTION

The present invention provides methods for the preparation of stable, unagglomerated, well dispersed, active-medical-agent core/shell nanocomposite particles having silane coupling agents such as but not limited to alkylamine or alkylcarboxylic acid silane coupling agents attached. A detailed discussion of the graft mechanism has been described elsewhere (Plueddemann, E. P., "Silane coupling agent," pp 29-48, Plenum Press, NY, 1982; Ung, T. et al., Langmuir, 14:3740-3748, 1998; Chiang, C. H., et al., J. Colloid Interface Sci., 74(2):396-403, 1980; Chiang, C. H. et al., J. Colloid Interface Sci., 86(1):26-34, 1982). The dispersion of the nanocomposites is achieved preferably by using high performance liquid chromatography (HPLC) to simultaneously wash and disperse the nanocomposite particles, in place of other techniques that involve sequential washing and dispersal steps.

The present invention also provides for the preparation of stable, dispersed nanocomposite particles to be used in vivo under physiological conditions, i.e. isotonic environment, by surface modification such as a carbodiimide-mediated polyethylene glycol (PEG) coupling agent to the silane coupling agent, which maintains their dispersed state. Other surface modification methods include dendrimers, amphiphilic agents, and charged adsorbates such as citrate as is known in the art. The present invention further provides for the attachment of binders, such as antibodies, thus enabling the nanocomposite particles to target specific sites for intracellular drug delivery.

The nanocomposite particles can include a variety of medically-active substances, such as organic fluorophores and therapeutic drugs, doped inside silica, titania, calcium phosphate or calcium phospho-silicate matrices. The synthesis techniques also can be modified to produce nanoparticles containing combinations of fluorophores and therapeutic medicinal agents. The intended biomedical application for the colloid of nanocomposite particles dictates the selection of core and shell-matrix materials.

The stable, well dispersed and unagglomerated active-medical-agent nanoparticles can be used for a variety of applications, such as, without limitation, pigments, fluorescent labeling, inks, slow release formulations, bioimaging, drug delivery, gene therapy and combinations thereof. For example, and within limitation, the nanoparticles of the present invention can be used as calcium deposition transporters, for medical diagnosis, and for medical therapeutics for cancer, infectious diseases, diabetes, cystic fibrosis and other diseases and disorders.

The fluorescent nanocomposite particles possess several qualities that make them particularly attractive for imaging and pigment applications, such as precise tunability of emission peaks, extended fluorescence lifetimes relative to traditional organic fluorophores, negligible photobleaching and self-quenching with the benefit of biocompatibility. Additionally, the nanoparticulate fluorescent emissions are not intermittent. Within the nanoparticle, direct contact between dye molecules and the environment is avoided, eliminating photodegradation of the fluorophore presumably because of absorption of the most energetic, and therefore, damaging of the excitation photons. As a result, the nanocomposite particles exhibit extended fluorescence lifetimes relative to traditional organic fluorophores or quantum dots as shown in FIGS. 3 through 5.

Nanocomposite particles can be used as a drug delivery system based on the encapsulation of a therapeutic agent in either a metal oxide shell with controlled porosity and/or a soluble outer shell/coating that on dissolution releases the therapeutic agent in the immediate vicinity of the afflicted area as shown in FIGS. 6 through 9. The protection of the therapeutic agent provided by the shell-matrix material allows for the delivery of drugs that are highly water-insoluble or unstable in physiological solutions. Furthermore, dissolution kinetics of the shell-matrix materials can be engineered to provide sustained release of therapeutic agents at target sites for extended periods of time.

The nanocomposite suspensions can also be used to deliver drugs including, but not limited to, ceramide, AZT, and dobutamine. Insulin can also be encapsulated in a soluble shell material such as calcium phosphate or calcium phospho-silicate. The surface can be modified to permit the nanocomposite particles to cross physiological membranes such as the gastro-intestinal tract, the blood-brain barrier, and cellular membranes. The targeted, time-controlled release can be used to deliver therapeutic agents such as insulin from the core-shell nanoparticles.

The nanocomposites also can be used in gene therapy for the delivery of therapeutic DNA to cells. The nanocomposite particles can offer increased stability of genetic material through encapsulation and improved uptake into target cells. Additionally, the nanoparticles can deliver genetic therapeutic agents in transcriptionally active forms while maintaining small sizes of less than about 200 nm.

Small particle size along with enhanced nanoparticle surface chemistry and dispersion contribute to the effectiveness of the nanocomposite particles. The small size achieved allows for evasion of capture by the reticuloendothelial system (RES) of animal models or the human body, permitting the nanoparticles to function in biological systems by crossing membranes such as the intestinal wall and the blood-brain barrier. Numerous biological barriers can be passed by the small nanocomposite particles, which allows for high concentrations of therapeutic agents to be delivered to target sites. In addition, the dispersed nanocomposite particles can be readily functionalized to deliver therapeutic agents directly to the targeted cells or tissues in the human body. Agglomeration compromises all the above biomedical applications as well as non-biomedical uses.

The synthesis of the nanocomposite particles is achieved using a reverse micelle system that includes water, a surfactant and a solvent, such as cyclohexane. The resultant size of the nanocomposites depends on the water-surfactant ratio, wherein a higher water-surfactant ratio produces larger nanocomposites. The present invention, therefore, provides for the synthesis of nanocomposite particles having a diameter of between about 1.0 to 100 nm, with a preferred diameter between about 1 and 20 nm, which is small enough to cross biological cell membranes. However, as defined below, the primary particle size obtained by the synthesis is not the actual size particle in suspension. Heretofore, nanocomposite particles prepared in reverse micelles have been agglomerated. The agglomeration occurs after synthesis during washing and collection operations for the nanoparticles. Thus, synthesis alone of primary nanoparticles is insufficient in providing well dispersed suspensions.

BRIEF DESCRIPTION OF THE DRAWINGS

FIG. 5 illustrates nanocomposite particle photodecay experimental results;

FIG. 6A-B is a phase contrast and a fluorescent image, respectively, of cultured vascular A7r5 smooth muscle cells that have taken up fluorescein/$SiO_2$ nanoparticles; and FIG. 6C-D is a phase image and a fluorescent image, respectively, of acutely isolated rat stellate ganglia neurons five days following intracardial injection of the nanoparticles;

FIG. 7A-B is a phase contrast and a fluorescent image, respectively, of in vitro (15 minute) exposure of stellate ganglion (SG) neurons to 0.002% $10^{-2}$ M rhodamine B/$SiO_2$ nanoparticles; FIG. 7C-D shows a phase image and a fluorescent image, respectively, of in vitro (15 minute) exposure of SG neurons to 0.002% $10^{-2}$ M fluorescein/$SiO_2$ nanoparticles; and FIG. 7E is a fluorescent image of fluorescein/SiO2-containing neurons in SG neurons seven days post-injection;

FIG. 12A-C is a schematic of the HPLC system used to wash and disperse nanopartices. FIG. 12A is the HPLC system; FIG. 12B is a TEM of Ag/$SiO_2$ nanoparticles; and FIG. 12C is a SEM of spherical silica beads in the stationary phase;

FIG. 13A-B illustrates a Ag/$SiO_2$ nanocomposite suspension (R=2, H=100, X=1) washed with centrifugation. FIG. 13A shows TEM analysis of the primary particle size. FIG. 13B shows the particle size distribution by dynamic light scattering;

FIG. 14A-B illustrates a Ag/$SiO_2$ nanocomposite suspension (R=2, H=100, X=1) washed with Soxhlet extraction. FIG. 14A shows TEM analysis of the primary particle size. FIG. 14B shows the particle size distribution by dynamic light scattering;

FIG. 15A-B illustrates a Ag/$SiO_2$ nanocomposite suspension (R=2, H=100, X=1) washed with sedimentation. FIG. 15A shows TEM analysis of the primary particle size. FIG. 15B shows the particle size distribution by dynamic light scattering;

FIG. 16A-B illustrates a Ag/$SiO_2$ nanocomposite suspension (R=2, H=100, X=1) washed with filtration. FIG. 16A shows TEM analysis of the primary particle size. FIG. 16B shows the particle size distribution by dynamic light scattering;

FIG. 17A-B illustrates the morphology of a Ag/$SiO_2$ nanocomposite suspension (R=2, H=100, X=1) washed with a conventional method. FIG. 17A shows TEM images of the core-shell structure. FIG. 17B shows the particle size distribution obtained from the TEM image.

FIG. 20A is two suspensions of nanocomposites, A and B. FIG. 20B shows digital images: suspension A, R=2, H=100, X=1, suspension, $D_{50}$=30 nm, SD=1.2 nm. B, R=8, H=100, X=1, $D_{50}$=20.3 nm, SD=1.5 nm. (With 95% confidence interval.) TEM images show the size, core-shell architecture and the state of dispersion of the suspensions A and B;

FIG. 26A-B illustrates the effect of pH on the state of dispersion for Ag/SiO$_2$ nanocomposite ethanol/water suspensions (R=8, H=100, X=1); FIG. 26A shows the particle size distribution by dynamic light scattering. FIG. 26B is TEM images taken by placing a drop of the suspension on a lacy carbon grid and dried at 25° C. Noted is the dissolution of the SiO$_2$ shell at pH 9.7, which gives rise to the bimodal distribution;

FIG. 27A-B is a transmission electron micrograph (TEM) image showing the size and morphology of organic core/silica shell nanocomposite particles containing rhodamine B as the organic core material at (A) low and (B) high; and FIG. 28 is a table shown as Table 1 and provides a list of silane coupling agents which are used for surface modification of the SiO$_2$-based nanocomposite particles.

DESCRIPTION OF THE PREFERRED EMBODIMENTS

The present invention provides for the first time a method for the synthesis of unagglomerated, highly dispersed, stable core/shell nanocomposite particles. Preferably, the nanocomposite particles have dispersing agents such as alkylamine or alkylcarboxylic acid silane coupling agents attached thereon, or the dispersing agent may be selected from the group consisting of citrate, oxalate, succinate and phosphonates, particularly in the synthesis of calcium-based nanoparticles. The dispersion of the nanocomposite particles is achieved by using a size exclusion high performance liquid chromatography (HPLC) system to simultaneously wash and disperse the nanocomposite particles.

The present invention also provides for the preparation of unagglomerated, well dispersed, stable nanocomposite particle suspensions for use in vivo under physiological conditions, i.e., isotonic environments, by surface modification such as a carbodiimide-mediated polyethylene glycol (PEG) coupling agent.

The present invention further provides for the formation of calcium-based shells such as calcium phosphate and calcium phospho-silicate shells onto the organic and/or inorganic cores that render the shells resorbable or biodegradable in vivo. The underlying shells can be porous or dense.

The present invention still further provides for the attachment of binders, such as antibodies and other functional groups including amine, carboxylate and synthetic polymers, with a wide variety of functionalities, thus enabling the nanoparticles to serve in delivery applications such as specific sites for intracellular drug delivery. Additionally, other moieties can be added to the surfaces of the nanocomposite particles, such as, without limitation, organic groups, metals, enzymes, macromolecules or plasmids. For example, a nanocomposite particle may contain a chemotherapeutic drug encapsulated in a time release shell surrounded by a target material such as folate that binds to cancer cells. The target material also can be used to transport proteins, enzymes, DNA, RNA and other compounds, which can enter the cells and/or nucleus of cells, which then are released therein.

Figure 1:
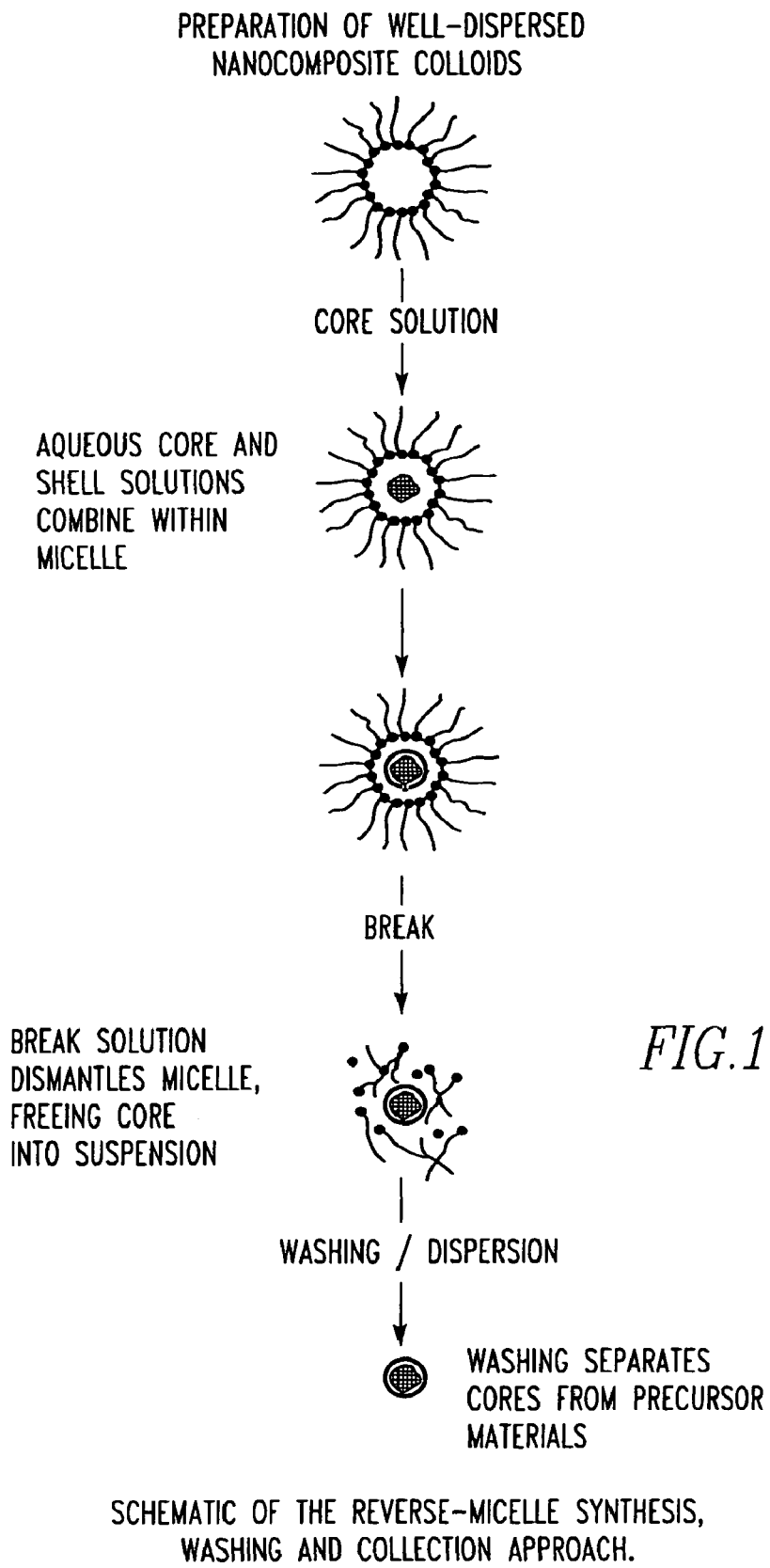
FIG. 1 is a schematic of the reverse-micelle synthesis, washing and collection approach of the present invention.
Figure 11:
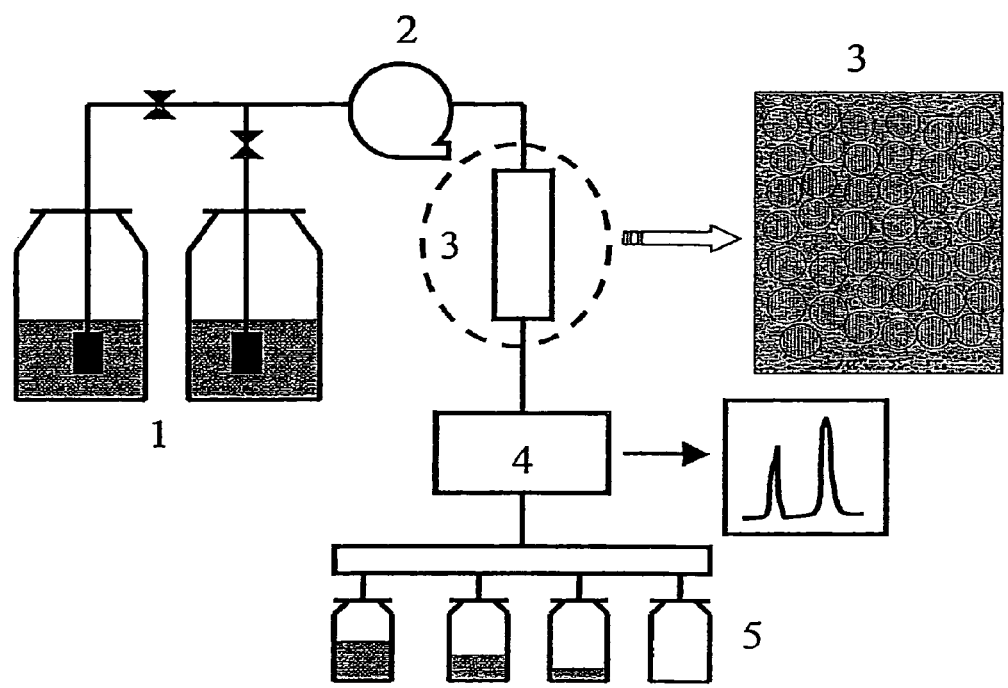
FIG. 11 is a schematic setup of the HPLC system for washing and dispersion of a Ag/$SiO_2$ nanocomposite ethanol/water suspension based on size exclusion chromatography. The UV-vis detector wavelength is set at 405 nm for the Ag/$SiO_2$ nanocomposites. The size of the HPLC column is HR 5/5 (5×50 mm)

The preparation of the well dispersed nanocomposite particles is achieved according to the methods of the present invention using a reverse micelle system which includes a surfactant, a hydrophobic solvent, an aqueous-based core precursor, such as an aqueous-based active-medical-agent precursor, fluorescent molecule, pigment, metal or other desired core materials, and a washing and dispersion method preferably using a size exclusion HPLC system (FIGS. 1, 11 and 12). The resultant size of the primary nanocomposite particles depends on the water-surfactant ratio, wherein a higher water-surfactant ratio produces larger nanocomposites. In particular, the size of the primary nanocomposite particles can be modified through the manipulation of processing parameters including the molar ratio of water to surfactant, the molar ratio of water to the shell precursor material, and for silica shell particles the molar ratio of base to the shell precursor material. The present invention, therefore, provides for the synthesis of nanocomposites having a diameter of between about 1.0 to 100 nm, preferably between about 1 to 20 nm, and most preferably about 10-20 nm. For example, a spherical SiO$_2$ nanocomposite particle approximately 10 nm in diameter can be synthesized when R=[water]/[surfactant]=2, H=[water]/[TEOS]=100, and X=[NH$_4$OH]/[TEOS]=1 is applied to the cyclohexane/water/Igepal® CO-520 system. It is believed that nanocomposite particles with diameters of about 20 nm or less are small enough to cross biological cell membranes, including the blood-brain barrier.

As used herein, the term "nanosize" refers to a special state of subdivision implying that a particle has an average dimension smaller than about 100 nm and exhibits properties not normally associated with a bulk phase, e.g., quantum optical effects.

As used herein, the terms "nanocomposite particles," "nanocomposites" and "nanoparticles" are interchangeable.

As used herein, the term "agglomeration" refers to the formation of an aggregate (a cohesive mass consisting of particulate subunits) in a suspension through physical (van der Waals, hydrophobic) or electrostatic forces. The resulting structure is called an "agglomerate."

As used herein, the term "unagglomeration," the antonym of "agglomeration," refers to a state of dispersion of an aggregate in a suspension.

As used herein, the term "aggregate" refers to a cohesive mass consisting of particulate subunits.

As used herein, the phrase "primary particles" refers to the smallest identifiable subdivision in a particulate system. Primary particles can also be subunits of aggregates.

An exemplary surfactant which can be used according to the methods of the present invention includes, without limitation, poly(oxyetheylene)nonylphenyl ether (Igepal® CO-520); surfactants, in combination with hydrophobic solvents and aqueous solutions that can also have low molecular weight hydrophobic solvents such as ethanol present that form water-in-oil, reverse micelles, are considered exemplary.

Exemplary shell precursors include, without limitation, SiO$_2$, TiO$_2$, ZnO, Fe$_2$O$_3$, ZrO$_2$, NiO and GeO$_2$, Sn, Pg, Ag and Au, tetraethoxysilane (TEOS), titanium (IV) isopropoxide, CaPO$_x$, CaCO$_3$, or calcium phospho-silicates having the general formula Ca$_x$(PO$_4$)$_3$(OH)$_z$(SiO$_2$)$_a$, where x, y, z and a can vary from zero to larger values.

Additionally, the core material can contain drug agents including, but not limited to, dobutamine, AZT, antibiotics, and ceramide and thus be used for infectious microorganisms, cancer or other foreign substances. Additionally, core materials can be composed of dehydrated hydrogels based on materials such as without limitation polyvinyl alcohol, polymethyl methacrylic acid, and 2-hydroxyethyl methacrylic acid. Further, the core material can be comprised of silica with a calcium phosphate coating. The calcium phosphate shell/silica core material can be well dispersed using agents such as citrate at physiological pH values (pH 6.5 to 7.4), thus, enabling the nanoparticles to be used as a therapeutic agent for tooth sensitivity via the release of calcium and phosphate into dentinal tubules upon delivery of the well-dispersed nanoparticles in suspension to the dentin of the tooth.

Additionally, the shell precursor material of the nanocomposite particles can contain cytotoxic agents selected from the group consisting of polyvinyl alcohol, polymethyl methacrylate and 2-hydroxylethyl methacrylate, and thus used as targets for infectious microorganisms, cancer or other foreign substances. Further, the shell precursor material can be comprised of a silica shell coating that includes calcium phosphate stabilized with citrate, thus enabling the nanoparticles to be used as a therapeutic for tooth sensitivity via the release of calcium into dentinal tubules upon delivery of the nanoparticles to the dentin of the tooth.

Exemplary aqueous core precursors also include, without limitation, metals such as Au, Ag, Co, Ni, Cu and Pt; semiconductors such as CdS; organic pigments; organic dyes; organic fluorophores, such as the sodium salt of fluorescein; rhodamine 123; rhodamine WT; rhodamine B and rhodamine B derivatives, such as rhodamine 123, fluorescein, fluorescein derivatives and luciferin; and/or active-medical-agents, such as therapeutic agents including those described in the penultimate paragraph above.

Figure 2:
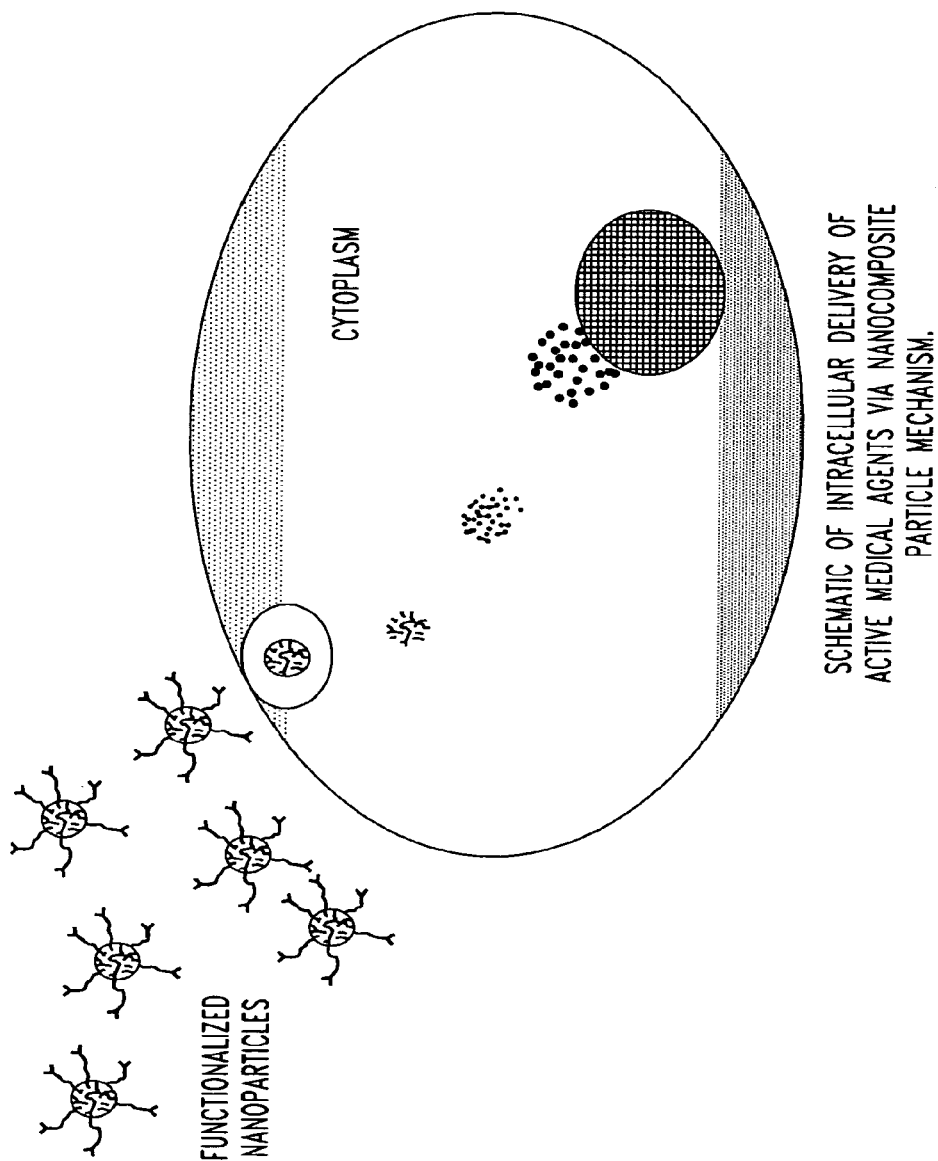
FIG. 2 is a schematic of intracellular delivery of active medical agents via nanocomposite particle mechanisms.

An exemplary therapeutic agent includes, without limitation, a genetic therapeutic agent, which can be used in gene therapy for delivery of therapeutic DNA or RNA (or any nucleic acids) to cells. The nanocomposite particles of the present invention offers increased stability of the genetic material via encapsulation and improved uptake into target cells (FIG. 2). Additionally, the nanocomposite particles can deliver genetic therapeutic agents in transcriptionally active forms while maintaining small diameter sizes of less than 100 nm.

Exemplary fluorescein and fluorescein derivatives include, without limitation, BDCECF; BCECF-AM; Calcien-AM; 5,(6)-carboxy-2',7'-dichlorofuorescein; 5,(6)-carboxy-2'7'-dichlorofuorescein diacetate N-succinimidyl ester; 5,(6)-carboxyeosin; 5,(6)-carboxyeosin diacetate; 5,(6)-carboxyfluorescein; 5-carboxyfluorescein; 6-carboxyfluorescein; 5,(6)-carboxyfluorescein acetate; 5,(6)-carboxyfluorescein acetate N-succinimidyl ester; 5,(6)-carboxyfluorescein N-succinimidyl ester; 5(6)-carboxyfluorescein octadecyl ester; 5,(6)-carboxynaphthofluorescein diacetate; eosin-5-isothiocyanate; eosin-5-isothiocyanate diacetate; fluorescein-5(6)-carboxamidocaproic acid; fluorescein-5(6)-carboxamidocaproic acid N-succinimidyl ester; fluorescein isothiocyanate; fluorescein isothiocyanate isomer 1; fluorescein isothiocyanate isomer 2; fluorescein isothiocyanate diacetate; fluorescein octadecyl ester; fluorescein sodium salt; napthofluorescein; napthofluorescein diacetate; or N-octadecyl-N'-(5 fluoresceinyl) thiourea (F18);

Exemplary rhodamine and rhodamine derivatives include, without limitation, 5,(6)carboxytetramethylrhodamine; 5-carboxytetramethylrhodamine N-succinimidyl ester; 6-carboxytetramethylrhodamine N-succinimidyl ester; 5,(6)-carboxytetramethylrhodamine N-succinimidyl ester; 5,(6)-carboxy-X-rhodamine; dihydrorhodamine 123; dihydrorhodamine 6G; lissamine rhodamine; rhodamine 110 chloride; rhodamine 123, rhodamine B hydrazide; rhodamine B; and rhodamine WT.

Exemplary organic pigments and dyes include, without limitation, hematoporphyrin dyes, such as 7,12-bis(1-hydroxyethyl)-3,8,13,17-tetramethyl-21H,23H-porphine-2 and 18-dipropanoic acid, and cyanine dyes and derivatives, such as indocyanine green; indoine blue; R-phycoerythrin (PE), PE-Cy 5; PE-Cy 5.5; PE-Texas Red; PE-Cy 7; Cy 3 NHS ester; Cy 3 maleimide and hydrazide; Cy 3B NHS ester; Cy 3.5 NHS ester; Cy 3 amidite; Cy 5 NHS ester; Cy-5; Cy 5 amidite; Cy 5.5; Cy-5.5 NHS ester; Cy 5.5 annexin V; Cy 7; Cy 7 NHS ester; Cy 7Q NHS ester; allophycocyanin (APC); APC-Cy 7; APC Cy 5.5; propidium iodide (PI); crystal violet lactone; patent blue VF; brilliant blue G; or cascade blue acetyl azide.

Exemplary silane coupling agents that can be added to the nanocomposite particles according to the method of the present invention include, without limitation, 3-aminopropyltrimethoxysilane (APS) (pH window 2.0~9.0; widely used to modify the surface of $SiO_2$); 3-aminopropylsilsesquioxane (pH window 2.0~6.5; adhesion promoter between silica particles and Ag nanoparticles); 3-glycidoxypropyltrimethoxysilane (GPS) (pH window<9.0; used to modify $SiO_2$ nanoparticles); trimethoxysilylpropyl-diethylenetriamine (DETA) (optimal pH 6.8; used for surface coating of $SiO_2$ nanoparticles); or 3-trimethoxysilylpropylsuccinic anhydride (pH window>8.0; used to provide negative charges on silica surfaces).

Additionally, alkylcarboxylic acid silane coupling agents can be added to the nanocomposite particles, such as amide-linked carboxyl groups (pH window<7.0; used to functionalize open end carbon nanotubes).

Further, surface modification such as a carbodiimide-mediated polyethylene glycol (PEG) coupling agent can be added to the silane coupling agent in order to use the nanocomposite particles in vivo in an animal or human. Dendrimer surface modification can also be used to promote the use of the nanocomposite particles in physiological environments.

Still further, binders, such as antibodies, can be attached, thus enabling the nanocomposite particles to target specific sites for intracellular drug and nucleic acid delivery.

Figure 20:
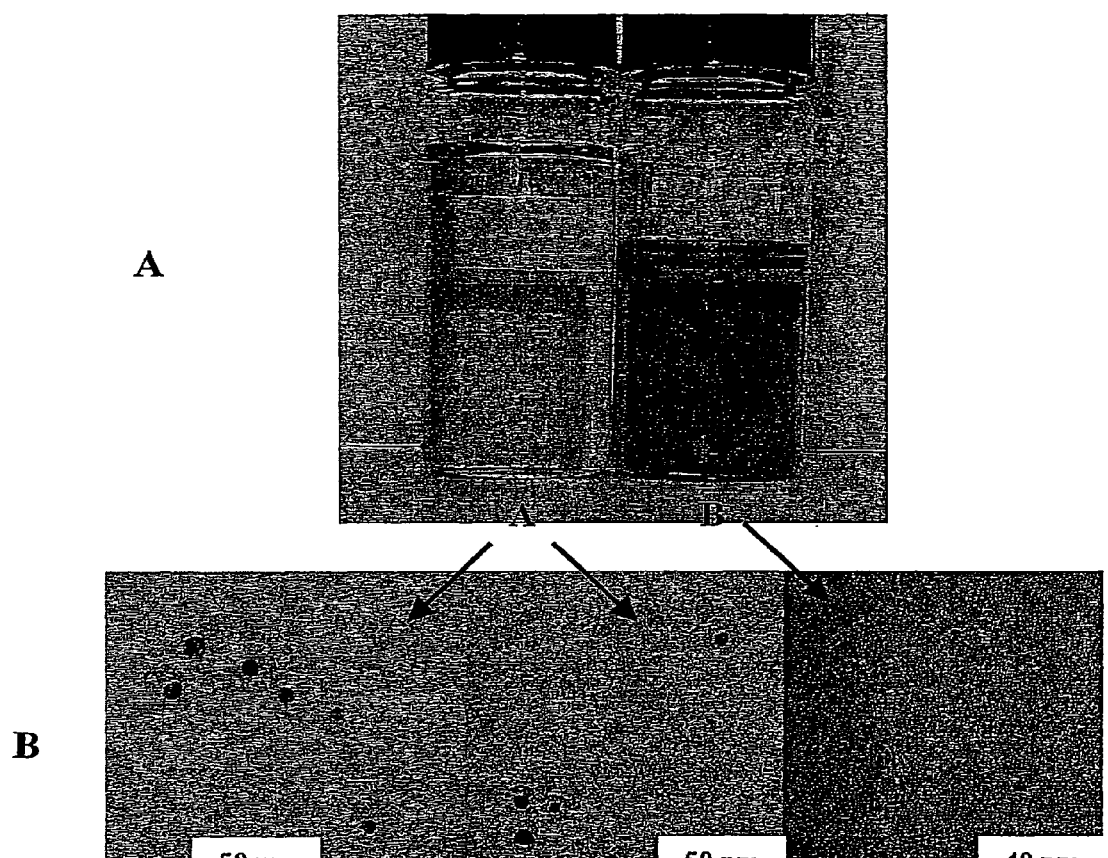
FIG. 20A-B illustrates the morphology of Ag/$SiO_2$ nanocomposite ethanol/water (7:3 vol) suspensions washed with HPLC.
Figure 21:
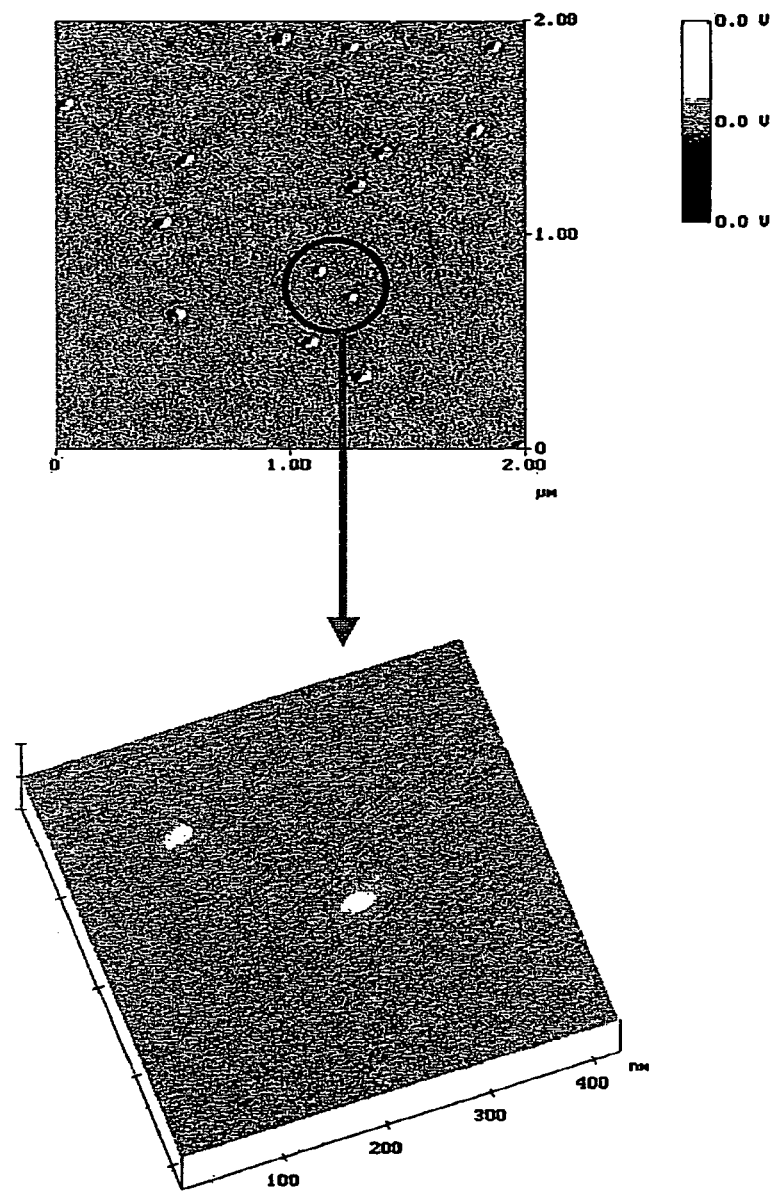
FIG. 21 shows AFM images of a Ag/$SiO_2$ nanocomposite (R=2, H=100, X=1) suspension obtained with the HPLC washing. Images were obtained by TAPPING MODE™. The samples were prepared by placing a drop of the Ag/$SiO_2$ ethanol/water suspension on a freshly cleaved mica substrate and spin coated at 1500 rpm for 30 s. The 3D image shoes the aggregate size of about 60 nm.
Figure 22:
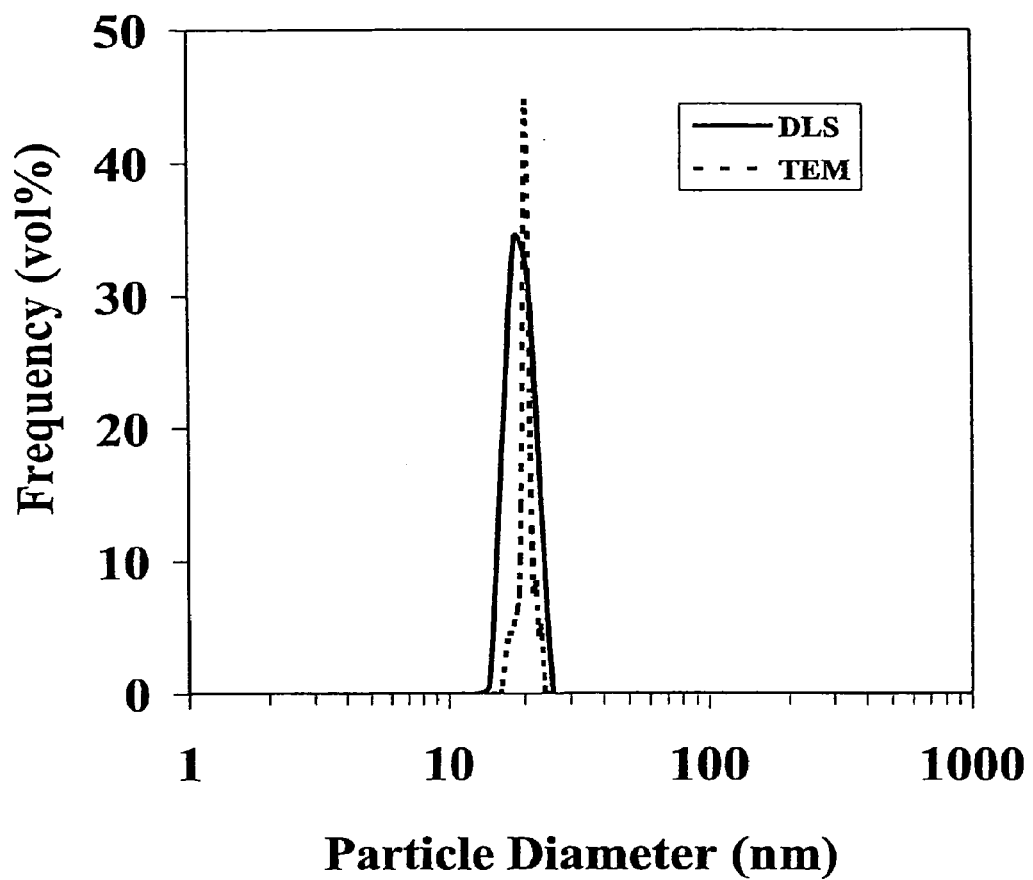
FIG. 22 illustrates the particle size distribution of Ag/$SiO_2$ nanocomposites (R=8, H=300, X=1) measured by dynamic light scattering (DLS) and TEM analysis. D50=18.6 nm, SD=1.5 nm for DLS, the particle size from TEM analysis is 20.3±1.5 nm (30 particles were counted). Noted is the close match between DLS and TEM analysis with AAN approximately equal to 1, indicating a well dispersed suspension.

The degree of successful dispersion of the nanoparticles, i.e., unagglomeration, can be estimated by computing an average agglomeration number (AAN) for a particular nanocomposite suspension (V. A. Hackley and Chiara F. Ferraris, "The use of nomenclature in dispersion science and technology," Special Publ. 960-3, National Institute of Standards and Technology, U.S. Department of Commerce, pp. 7-8, August 2001, Superintendent of Documents, U.S. Government Printing Office, Mail Stop SSOP, Washington, D.C., 20402-0001). The AAN is defined as the average number of primary particles contained within an agglomerate. It can be calculated as the ratio of the median particle volume determined via quasi-electric light scattering (QELS) to the microscopic particle size volume determined through transmission electron microscopy (TEM) characterization. In particular, AAN is calculated from the ratio of the median particle size, as determined by, for example, dynamic light scattering, sedimentation or electrical zone sensing techniques, to the average equivalent spherical volume ($V_{BET}$) given by the BET gas adsorption method, such that:

$$AAN = \frac{V_{50}}{V_{BET}} = \left(\frac{D_{50} \cdot SSA \cdot \rho}{6}\right)^3$$

where $V_{50}$ is the equivalent spherical volume calculated from the median diameter, $D_{50}$ is μm, SSA is the specific surface area in $m^2/g$ and $\rho$ is the particle density in $g/cm^3$. Based on our experience, an AAN less than 10 is a well dispersed suspension; an AAN from $\geq$10 to 30 is a moderately dispersed suspension, and an AAN greater than 30 is a poorly dispersed suspension. A discrepancy sometimes can be observed in particle sizes provided by QELS and TEM due to QELS measurement of the electrical double layer surrounding each of the nanocomposite particles, however a standard protocol for QELS characterization of nanocomposite colloidal suspensions has been developed by the inventors to minimize hydrodynamic radius effects due to double layer sensitivity. As shown in FIGS. 20-22, the the present technology permits the reliable preparation of nanocomposite particle suspensions with AAN<10.

Figure 3:
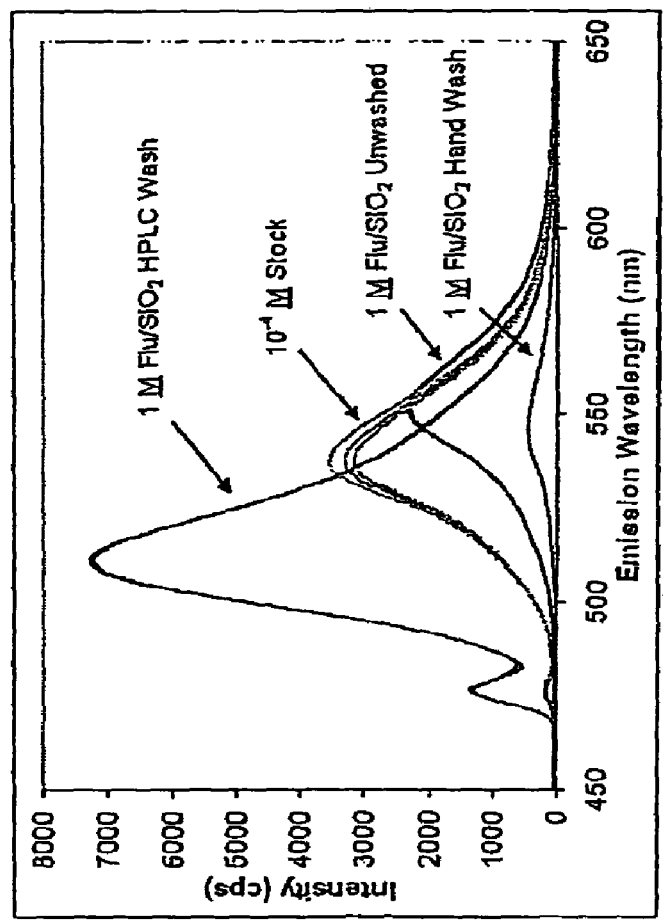
FIG. 3 shows fluorescent emission scans of fluorescein/$SiO_2$ nanoparticles.
Figure 4:
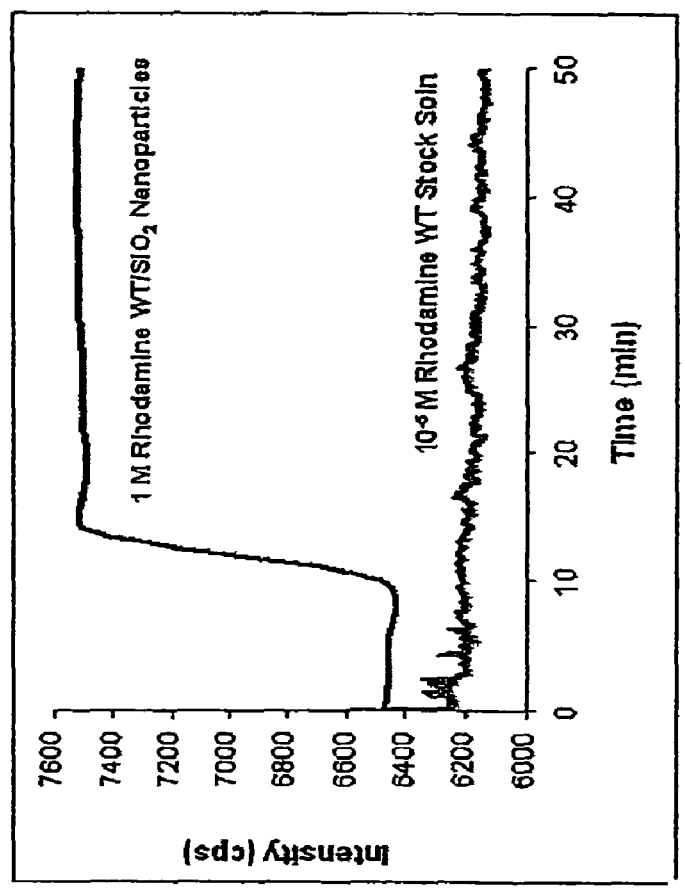
FIG. 4 shows fluorescent emission timescans of 1 M rhodamine WT/$SiO_2$ nanocomposite particles and $10^{-5}$ M rhodamine WT stock solution.
Figure 6:
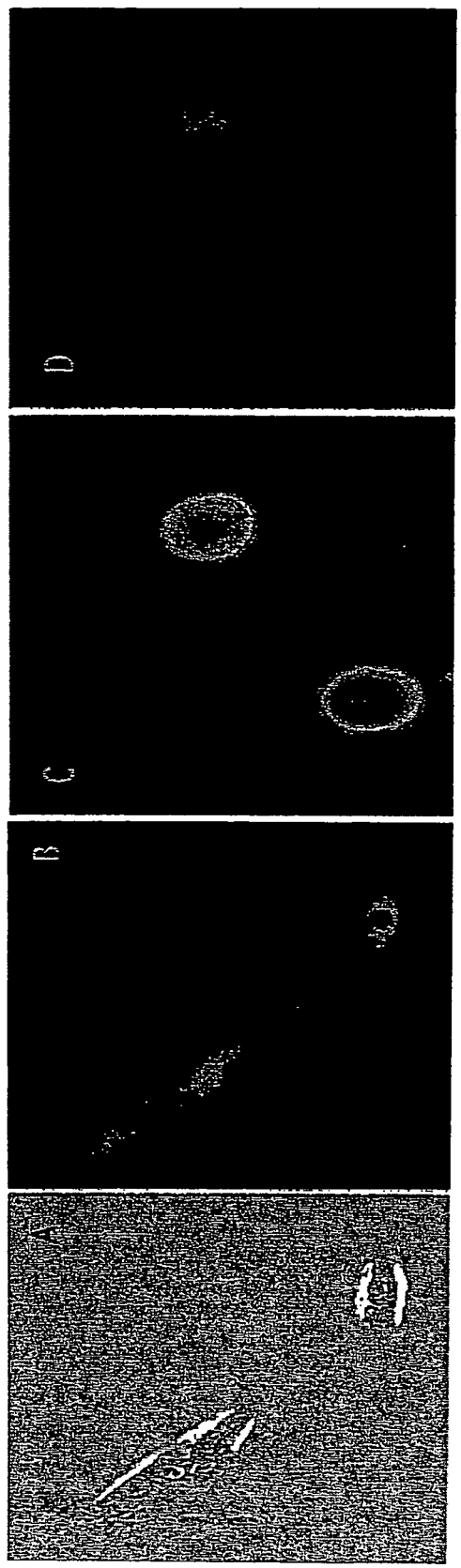
FIG. 6A-D shows phase contrast and fluorescent images of smooth muscle cells and rat stellate ganglia.
Figure 7:
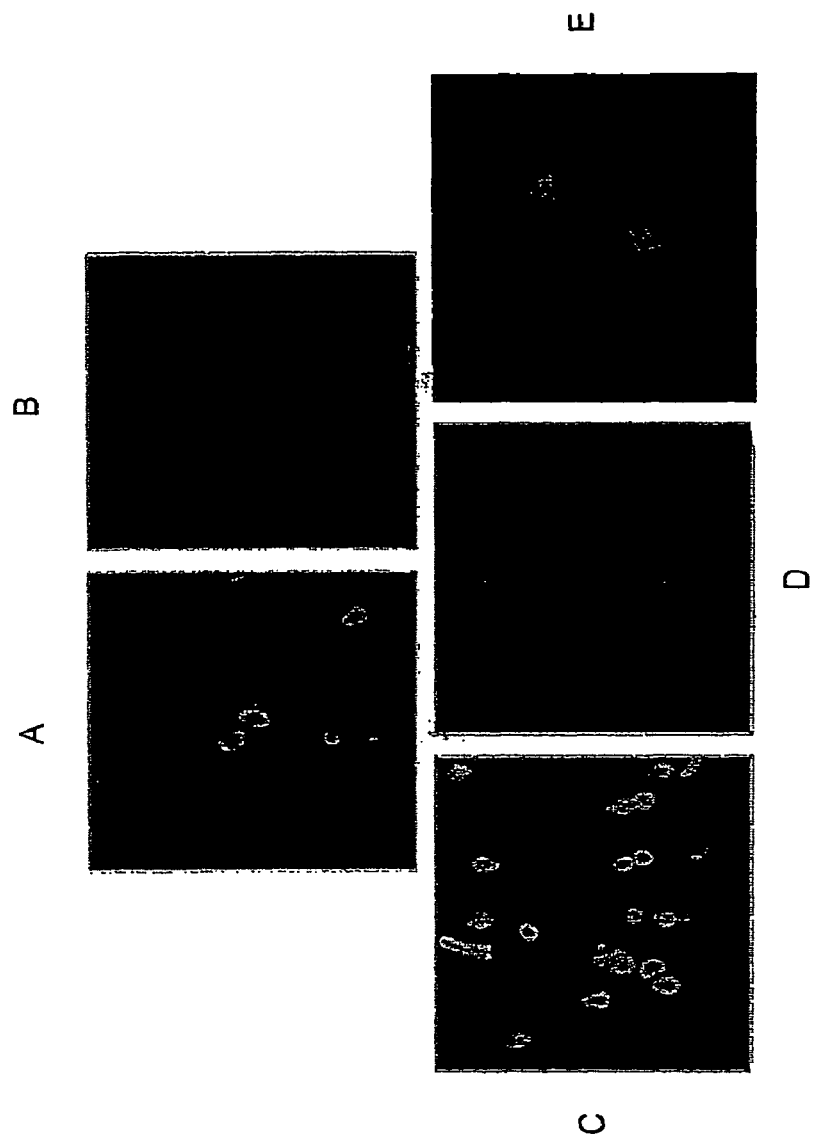
FIG. 7A-E shows phase contrast and fluorescent images of rat stellate ganglia.

In one embodiment of the present invention, rhodamine B/$SiO_2$ and fluorescein/$SiO_2$ nanocomposites are synthesized according to the methods of the present invention which have the ability to circumvent various functional limitations encountered by traditional organic dyes in biotechnical applications. For example, they exhibit strong size-dependent emission spectra due to quantum size effects (FIGS. 3 and 4, respectively). Further, the nanoparticles have virtually continuous excitation spectra above the threshold for absorption. As a result, the nanocomposite particles may be used as exceptional luminescent probes in biological tagging technologies. Indeed, the rhodamine B/$SiO_2$ and fluorescein/$SiO_2$ nanoparticles are superior to existing organic chromophores in many arenas. For example, the rhodamine B/SiO2 and fluorescein/$SiO_2$ nanoparticles possess high quantum yield and high resistance to photodegradation (FIG. 5). Additionally, photoluminescence from the nanocomposite particles may be detected at concentrations equivalent to concentrations encountered for organic dyes, thus enabling the use of conventional fluorescence methods, with the added benefit of biocompatibility. The nanocomposite particles of the present invention thus can alleviate the inadequacies of current medical technologies. For example, one application for the fluorescent nanoparticles of the present invention is to illuminate the interior of living cells, such as smooth muscle cells (FIG. 6A, B) or neurons (FIGS. 6C, D and 7A-E). Live-cell staining using organic dyes is a widely accepted practice, but the cells need to be saturated with a large amount of dye molecules, otherwise the stain eventually bleaches due to photophysical degradation. The rhodamine 123/$SiO_2$ and fluorescein/$SiO_2$ nanoparticles solve this problem because they possess a high resistance to photodegradation due to the protection of the fluorescent core provided by the silica shell. It is believed, without being bound by the theory, that the inorganic shell is responsible for the maintenance of nanoparticle fluorescence, which lasts up to and beyond seven months. Further, the nanocomposite particles synthesized according to the methods of the present invention exhibit inhibited and/or severely reduced photobleaching, as shown in FIG. 3, as well as having lifetimes in excess of about six months.

Additionally, nanocomposite particles may be used as "tracer bullets" for chemical assays. For example, the nanocomposite particles can contain dessicated hydrogels that are encapsulated with calcium phosphate, which can circulate throughout the body and swell with water. Nanocomposite particles that are approximately 20 nm in diameter are able to pass through cell membranes, such as glomerular cells of Bowman's capsule of the kidney. Thus, they can be excreted in the urine, after which their contents may be analyzed.

Figure 8:
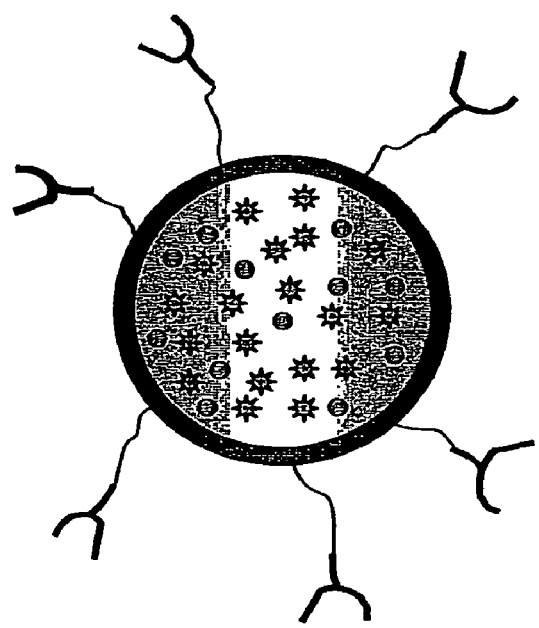
FIG. 8 is a schematic of a functionalized nanocomposite particle containing an organic fluorophore and a therapeutic drug.

The nanocomposite particles of the present invention can be used for systemic delivery of hydrophobic therapeutic drugs, which normally are not transportable through the circulation (FIG. 8). Furthermore, because nanocomposite particles of 20 nm or less in diameter can cross the blood-brain barrier, the delivery of drugs directly into the central nervous system can be achieved. Nanocomposite particles comprised of a porous silica coating or calcium phosphate can be used to encapsulate hormones, such as insulin. Such nanocomposite particles can cross the microvilli of the intestinal lumen but do not cross through glomerular cells of tubules. The nanocomposite particles thus can provide a feedback mechanism for insulin release, in which pyruvate produced as a result of glucose metabolism binds to the calcium phosphate shell of the nanoparticles and promotes insulin release from the nanoparticles. Furthermore, the nanocomposite particles can be targeted specifically for pancreatic cells, thereafter releasing insulin within the pancreas.

Another application for the nanocomposite particles of the present invention includes the use of calcium phosphate (CP) or calcium phospho-silicate (CPS)-coated silica particles as agents to induce biomineralization. For example, the use of CP or CPS shell-silica core particles can be used in toothpaste for incorporation in exposed dentinal tubules, which will induce biomineralization and promote closure of the tubules, thus mitigating hypersensitivity in teeth.

Figure 9:
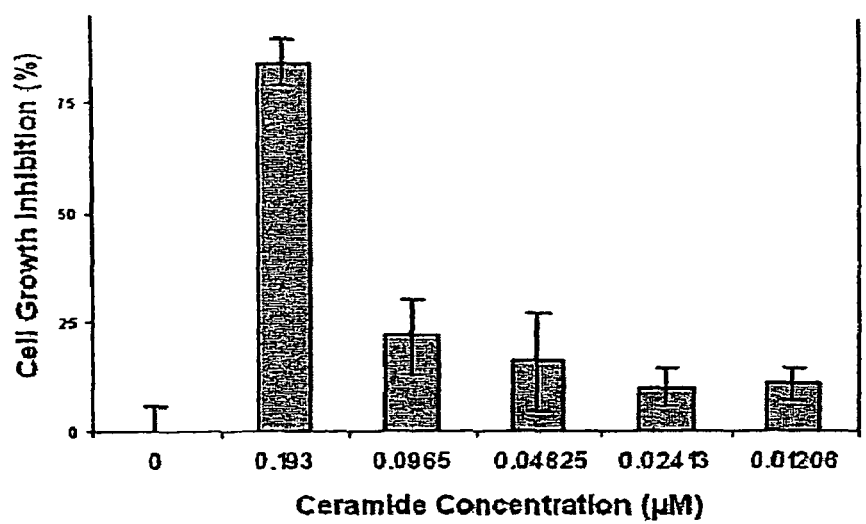
FIG. 9 is a bar graph illustrating that ceramide/$Ca_{10}(PO_4)_6(OH)_2$ nanoparticles induce human coronary artery smooth muscle cell growth inhibition.

Other examples of applications for the resorbable shell nanocomposite particles include incorporation of drugs such as dobutamine, 3'-azido-3'-deoxythymidine (AZT) used in AIDS therapy, and ceramide used as a chemotherapeutic agent for cancers or for inhibiting coronary smooth muscle cell growth for either systemic or targeted delivery to specific cells or tissue (FIG. 9).

Other applications for the fluorescent nanoparticles of the present invention include, without limitation, fluorescent tagging to examine capillary flow; defining neuronal cell connectivity; studying dye translocation through gap junctions; and use for tracking septic disposal systems as well as other water transport studies.

In another embodiment of the present invention, a method of preparing nanocomposite particles in suspension using a water-in-oil synthesis protocol is provided comprised of preparing a reverse micelle microemulsion containing nanocomposite particles, treating the reverse micelle microemulsion with a silane coupling agent, breaking the microemulsion to form a suspension of the nanocomposite particles by adding an acid/alcohol solution, such as acetic acid/ethanol, to the microemulsion maintained at a desired pH of between about 6 and 8, and simultaneously washing and dispersing the suspension of nanocomposite particles. The reverse micelle is prepared by forming a mixture comprised of an amphiphilic surfactant such as poly(oxyethylene) nonylphenylether (marketed as Igepal® CO-520), a hydrophobic solvent such as cyclohexane, and an aqueous based solution (with or without hydrophilic organic co-solvent present as desired), with the mixture agitated at 25 degrees C. for a time sufficient to produce a stable homogeneous, water-in-oil, reverse micelle. Typical times for agitation range from 5 minutes to 24 hours with a preferred time of 30 minutes. If desired, particularly for silica and titania shell materials, base including but not limited to $NH_4OH$ or tetraethylammonium hydroxide is added with the resulting suspension agitated for additional time from 2 minutes to 24 hours. The optimal maturation time for the nanocomposite materials depends on the shell material. For silica and titania shell nanocomposites, 24 hours is preferred; for calcium phosphate, calcium phosphosilicate, and other calcium-based dispersal methods for the nanocomposite particles must begin after a preferred time of 2 minutes to prevent irreversible agglomeration. A dispersing agent, such as APS, is then added to the suspension to modify the surface charge of the nanoparticles. The microemulsion is broken by rapidly stirring with a solution that breaks the reverse micelles forming a reasonably homogeneous solution. A preferred breaking solution is composed of acetic acid and ethanol. It has been determined that an aqueous solution cannot be used effectively to break microemulsions of the cyclohexane/Igepal® CO-520/water system of the present invention.

In a further embodiment of the present invention, a method is provided for synthesizing titania nanocomposite particles, comprised of preparing a reverse micelle microemulsion by forming a mixture comprised of the surfactant, such as poly (oxyetheylene)nonylphenyl ether (Igepal® CO-520), hydrophobic solvents such as cyclohexane and an aqueous precursor at room temperature, stirring the mixture for a preferred time of about 30 minutes, adding base to form a suspension, stirring the suspension for about 15 minutes and adding the shell precursor titanium (IV) isopropoxide (TIPO). Full maturity of the micelles occurs about 24 hours after the addition of TIPO. A silane coupling agent or simple adsorbate such as citrate solution is added to the suspension to modify nanoparticle surface charge prior to breaking the microemulsion with an acetic acid/ethanol solution.

In still another embodiment of the present invention, a method is provided for synthesizing calcium phosphate nanocomposite particles, comprised of an active-medical-agent core and a $Ca_{10}(PO_4)_6(OH)_2$ shell in which two separate microemulsions are prepared with Igepal® CO-520, cyclohexane and an aqueous solution containing the precursor serving as the basis for the microemulsions. Calcium chloride dihydrate and sodium dihydrogenphosphate serve as the precursors for the calcium phosphate shell. Sodium metasilicate is added to induce nucleation in selected systems. In particular, two microemulsions, each containing specific amounts of Igepal® CO-520, cyclohexane and aqueous precursor solutions, are prepared by rapidly mixing at ambient temperature. The microemulsions are allowed to mix for about 5 minutes. Microemulsion #2 is added drop wise to Microemulsion #1. The micelles are allowed to mature for about 2 minutes. A dispersant in the form of a silane coupling agent or citrate solution is added to the suspension to modify nanoparticle surface charge.

In a further embodiment of the present invention, a method is provided for synthesizing calcium phospho-silicate (CPS) nanocomposite particles, comprised of an active-medical-agent core and a $Ca_{10}(PO_4)_6(OH)_2$ shell in which two separate microemulsions are prepared with Igepal® CO-520, cyclohexane and an aqueous solution containing the precursor serving as the basis for the microemulsions. Calcium chloride dihydrate and sodium dihydrogenphosphate serve as the precursors for the calcium phosphate shell. Sodium metasilicate is added to induce nucleation in selected systems. In particular, two microemulsions, each containing specific amounts of Igepal® CO-520, cyclohexane and aqueous precursor solutions, are prepared by rapidly mixing at ambient temperature. The microemulsions are allowed to mix for about 5 minutes. Microemulsion #2 is added drop wise to Microemulsion #1. The micelles are allowed to mature for about 5 minutes, after which $NH_4OH$ and then TEOS is added. A silane coupling agent then is added to the suspension to modify the surface charge. The microemulsion is broken while rapidly stirring with 50 mL of 0.02 M acetic acid/ethanol solution. The microemulsion is broken while rapidly stirring with an acetic acid/ethanol solution.

The methods of the present invention also include simultaneously washing and dispersion of the nanocomposite particles comprised of using a size-exclusion HPLC system which includes an HPLC column of approximately 5×50 mm, packed with spherical silica beads of about 1 μm to about 100 μm, preferably about 20 μm in diameter. Dehydrated ethanol, which is pH adjusted to the particular nanoparticulate system, is pumped through the HPLC to wet the column packing before the nanoparticle suspension is introduced. The nanoparticle suspension then is pumped into the HPLC system through a stationary phase that can be comprised of microspheres treated with a silane coupling agent at a flow rate of about 1 mL/min to about 100 mL/min, preferably about 1 mL/min. The HPLC packed column out-flow is connected to detectors in order to measure changes in UV absorbance or fluorescence. The detectors monitor and distinguish when the column is fully saturated with nanoparticles. The particles then are eluted and redispersed using an ethanol/distilled water solution of up to about 250 v/o water, preferably about 70 v/o water.

Washing involves the removal of residual precursor materials and excess active-medical-agents while maintaining nanoparticle dispersion. Washed particles are more easily and accurately characterized due to the absence of residual organics interfering with techniques such as transmission electron microscopy (TEM) and quasi-elastic light scattering (QELS). Washing nanoparticles for biological applications is a critical step since surfactants and other organic materials have detrimental toxicological effects. The dispersion scheme involves the application of protection-dispersion theory to the nanoparticle suspensions. Dispersion of the nanocomposite particles is further enhanced by the use of size-exclusion high performance liquid chromatography (HPLC) to simultaneously wash and disperse the nanocomposite particles.

The size-exclusion HPLC system and method as taught in the present invention generates unagglomerated, stable nanocomposite particle suspensions superior to other particle recovery techniques such as sedimentation, centrifugation or Soxhlet extraction. The HPLC washing procedure is a modification of the analytical technique used for the separation of complex liquids. The HPLC washing method thus allows for the automated removal of surfactants, residual precursor materials, and unencapsulated active-medical-agents. The separation of the nanoparticles from the waste-containing carrier solution is achieved due to differences in the interactions of the mobile and stationary phases.

The HPLC washing and dispersion process is influenced by variables including surface modification of the mobile and stationary phases, suspension pH, elutant solution composition, flow rate and column dimensions. Typically, nanocomposite particle suspensions between about 10 to 20 w/o solids loading are obtained after HPLC washing, as measured by acoustic methods (Anton Paar, DMA 35N, Graz, Austria).

The present invention is more particularly described in the following examples, which are intended to be illustrative only, because numerous modifications and variations therein will be apparent to those skilled in the art.

EXAMPLE 1

Synthesis and Dispersion of $Ag/SiO_2$ Nanocomposite Particles Using HPLC Compared to Four Conventional Techniques 1. Materials and Methods
Synthesis The method used to synthesize the $Ag/SiO_2$ nanocomposite particles has been described previously by Li, T. et al. (Langmuir, 15[13]:4328-4334, 1999). All chemicals involved were used as received. Nonionic surfactant poly (oxyethylene) nonylphenyl ether (Igepal CO-520), cyclohexane, silver nitrate, tetraethoxysilane (TEOS), silane coupling agent 3-aminopropyltriethoxysilane (APS), hydrazine and $NH_4OH$ (28~30%), were all purchased from Aldrich Chemicals Co. (Milwaukee, Wisc.). Dehydrated ethanol (200 proof, Pharmca Products, Inc., Brookfield, Conn.) and glacial acetic acid (J. T. Baker Chemicals) were used without further purification. All aqueous stock solutions were prepared with deionized water (specific conductivity=$0.4 \times 10^{-7}$ S/m).

Figure 10:
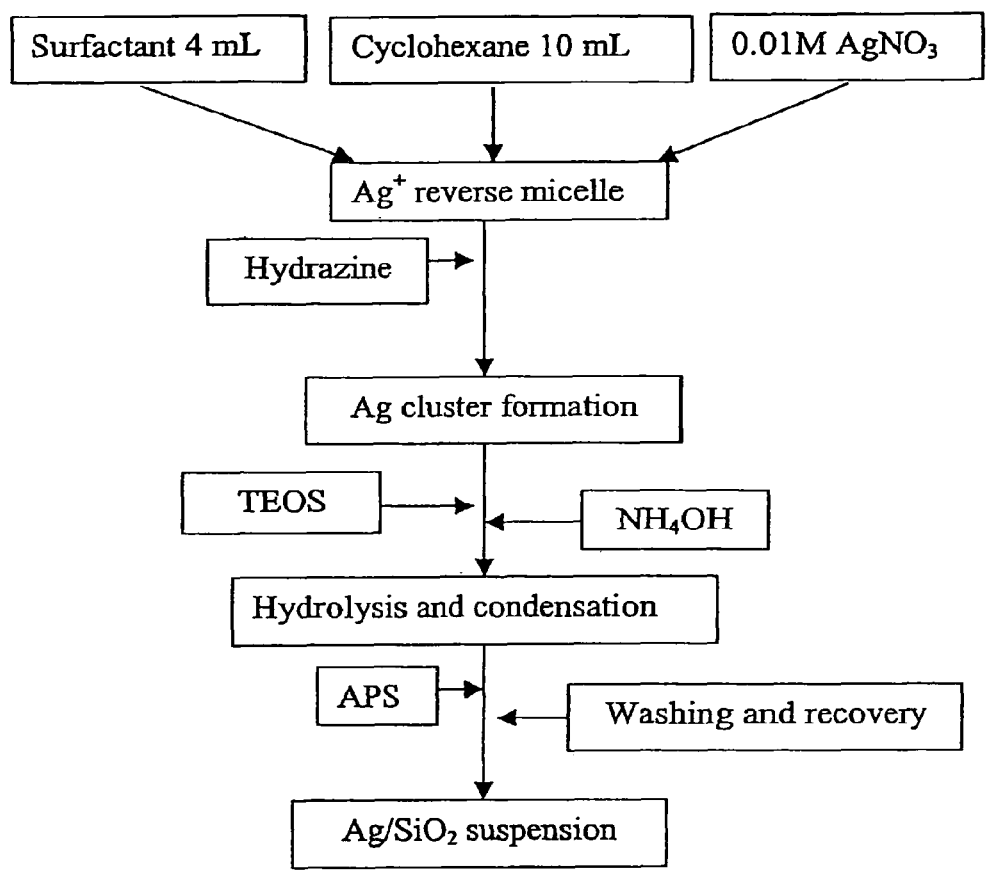
FIG. 10 is a flow sheet of a Ag/$SiO_2$ nanocomposite suspension obtained from reverse micelle synthesis and washing with various methods.

Briefly, the reverse micelle was formed by mixing 10 ml of cyclohexane and 4 ml of Igepal CO-520 followed by adding a certain amount of 0.01 M $AgNO_3$ aqueous solution under vigorous stirring according to the R ratio. The $Ag^+$ ions were reduced to metallic Ag by adding a drop of hydrazine into the microemulsion. An appropriate amount of TEOS was added to coat the metal cluster based on the H ratio, and a drop of $NH_4OH$ aqueous solution was introduced as catalyst to ensure the hydrolysis of TEOS in an alkaline pH range. The microemulsion was sealed and settled for 24 hours for the completion of the $SiO_2$ coating under stirring. The reverse micelle microemulsions containing the $Ag/SiO_2$ nanocomposite particles were then treated with an APS-ethanol solution. The surfaces of the $Ag/SiO_2$ nanocomposite particles were positively charged (~30 mV) at a pH lower than about 7.0 due to the surface grafting of APS. The microemulsion was broken with 50 ml of 0.02 M acetic acid/ethanol stock solution with rigorous stirring to maintain the pH below 7.0. The suspension was processed further with ethanol using an HPLC washing technique. Four other conventional techniques, centrifugation, soxhlet extraction, sedimentation and filtration, also were used to compare the effectiveness of the HPLC technique with respect to dispersion of the nanocomposite particles. The complete process is shown in FIG. 10. The residual concentration of surfactant Igepal CO-520 was monitored by UV-vis spectra. Using the Beer-Lambert law, a calibration curve for Igepal CO-520 was constructed by measuring the absorbance at 280 nm as a function of concentration.

Washing with HPLC

Reverse micelle microemulsions containing $Ag/SiO_2$ nanocomposite particles were treated first with an APS-ethanol solution (1 w/o, 15 g of APS mixed with 15 mL anhydrous ethanol, 0.15 mL glacial acetic acid and 0.75 μL DI water). The surfaces of the $Ag/SiO_2$ nanocomposite particles were positively charged (~30 mV) at a pH lower than 7.0 due to the surface grafting of APS. The microemulsion was broken with 50 ml 0.02 acetic acid/ethanol stock solution with rigorous stirring to maintain the pH below pH 7.0. The suspension then was pumped into the HPLC system (Waters Delta Preparation 3000 HPLC system, Milford, Mass.). An empty HR 5/5 column was purchased from Amersham Pharmacia Biotech, Piscataway, N.J.). The column was packed with 20 μm APS-treated spherical silica beads (Stellar Phases, Inc., PA) at a rate of 2 mL/min. The terminal of the column was connected to a UV-vis spectrum detector set at a wavelength of 405 nm, the wavelength of the surface plasmon peak of the Ag quantum dot core. Dehydrated ethanol was pumped through the HPLC system as the washing solvent and the nanocomposites were collected with an ethanol-water solution (volume ratio 7:3). A fraction collector was utilized to collect elute from the HPLC column during the entire washing procedure. A sketch of the configuration for the HPLC system is shown in FIG. 11. A schematic of the HPLC system is shown in FIG. 12A, which includes a transmission electron micrograph (TEM) of Ag/SiO2 nanoparticles (FIG. 12B) and a scanning electron micrograph (SEM) of the spherical silica beads in the stationary phase (FIG. 12C).

Characterization

The zeta potentials of $Ag/SiO_2$ nanocomposite suspensions were measured by a Zeta PALS Analyzer based on the dynamic light scattering principle (Brookhaven Instruments Co., NY). The pH was adjusted by 0.1 M $HNO_2$ and 0.1 M KOH aqueous solutions. The morphology and dispersibility of the $Ag/SiO_2$ suspensions were first examined with an atomic force microscope (AFM) (MultiMode, Digital Instruments) with the tapping mode. The samples for AFM experiments were prepared by placing drops of $Ag/SiO_2$ suspension on a freshly cleaved mica substrate and spin coating the substrate at 1500 rpm for 30 sec. Image analysis was performed on a high-resolution transmission electron microscope (HRTEM) (HF 2000, Hitachi, Japan and JEOL 2010F, Tokyo, Japan). A drop of freshly prepared suspension was added on a carbon film supported on a copper grid and dried overnight in a vacuum oven. A state-of-the-art Malvern Nanosizer (Malvern Instruments, UK) was used to determine the state of dispersion for the $Ag/SiO_2$ suspension. The morphology of as-received $SiO_2$ microspheres was obtained by a scanning electron microscope (SEM, Hitachi S-3000H, Japan). The surface structure of $SiO_2$ microspheres was examined by AFM after a washing and dispersion cycle. All the pH measurements were carried out with a Sentron pH meter (Argus IP 65 ISFET probe, Sentron, Inc., WA) calibrated against standard aqueous buffer solutions.

2. Results and Discussion

Dispersion and Morphology of $Ag/SiO_2$ Nanocomposite Particles Using Four Conventional Techniques (a) Centrifugation The state of dispersion for $Ag/SiO_2$ nanocomposites washed and redispersed with centrifugation is shown in FIG. 11A-B. For the sample with R=2, H=100 and X=1, the primary particle size by TEM was 30±1.2 nm (FIG. 11A). The collective particle size distribution measured by dynamic light scattering was 233 nm (FIG. 11B). Using the average agglomeration number (AAN) concept developed by Adair et al. (Advances in Ceramics, 111, pp 142-156, The American Ceramic Society, OH, 1984), the AAN of the $Ag/SiO_2$ suspension was calculated by taking a volume ratio of the light scattering size (DLS) to the microscopic size (TEM). For the centrifugation protocol, the AAN was estimated to be 468, indicating a considerably aggregated suspension. This was consistent with the TEM observation.

(b) Soxhlet Extraction

Soxhlet extraction offers a pathway to wash and extract materials in a continuous manner, which improves the efficiency of the washing solvent. $Ag/SiO_2$ nanocomposites were washed and collected with a soxhlet extractor. The washing solvent was heated to its boiling point and evaporated from the solvent reservoir, then condensed down to the thimble which contained as-prepared $Ag/SiO_2$ nanocomposites, and finally flowed back into the reservoir. The washing cycle lasts for about 40 min. FIG. 4A-B shows a TEM image as well as particle size distribution of the $Ag/SiO_2$ nanocomposites washed with the soxhlet extractor. The AAN was determined to be around 106, which was confirmed by TEM analysis (FIG. 12A). A portion of the $Ag/SiO_2$ nanocomposites displayed a particle size less than 10 nm, which may have been caused by the dissolution of the $SiO_2$ shell during washing (FIG. 12B).

(c) Sedimentation

The $Ag/SiO_2$ nanocomposites were washed with sedimentation after APS coating. Compared to the particle size from TEM (FIG. 13A), the AAN was estimated to be 921. Although the AAN was high relative to that of centrifugation, the dispersion may be further improved by using filtration to remove the nanocomposite agglomeration. However, this washing procedure is usually time-consuming even though the protocol requires little instrumentation. The nanocomposite suspension demonstrated bimodal distribution according to the light scattering analysis, with a primary mode at around 25 nm and a secondary mode at 2 μm (FIG. 13B).

(d) Filtration

The filtration washing method follows the protocol reported by Tan, W. et al. (U.S. Pat. No. 6,548,264, 2003, entitled "Coated Nanoparticles") and Zhao, X. et al. (Adv. Mater., 16:173-176, 2004). The microemulsion was broken and coagulated with acetone, and then the nanocomposites were filtered (2 μm filter, Millipore, Bedford, Mass.) and washed with acetone and ethanol three times. The Tan et al. protocol does not control pH levels of the nanocomposite suspension to below pH 7, and preferably to between about pH 6 to 7, which is necessary to prevent agglomeration. The Tan et al. protocol therefore resulted in an irrreversible agglomeration of the nanocomposite particles, as shown in FIG. 14A. The resultant particle size distribution measured by dynamic light scattering was bimodal (FIG. 14B), and the agglomeration size was about 250 nm. The AAN for the Ag/$SiO_2$ nanocomposite ethanol suspension was about 318. The agglomeration most likely occurred because of the coagulation induced by the acetone, which allowed the nanocomposite contacts to form and grow.

FIG. 15A-B shows the morphology of Ag/$SiO_2$ nanocomposites derived from water-in-oil reverse micelle synthesis using four conventional washing protocols. The formation mechanism and chemical kinetics of nanocomposites in the cyclohexane/Igepal/water reverse micelle system has been discussed previously in detail by Arriagada, F. J. et al. (J. Colloid Interface Sci., 211:210-220, 1999; Colloids and Surfaces A, 154:311-326, 1999; J. Colloid Interface Sci., 218: 68-76, 1999). The conventional methods used to wash and collect as-synthesized nanocomposite particles was unable to prevent agglomeration induced by van der Waals forces between particles, as clearly illustrated in the TEM images (FIG. 15A).

The sizes and shapes of the nanocomposites generated from the reverse micelle synthesis depend on the molar ratio of water to surfactant R and the ratio of water to TEOS H. The general trend for the growth of Ag/$SiO_2$ nanocomposites is that the silver core diameter is proportional to R, while the silica shell thickness decreases as H increases. With R=2, H=100, and X=1 ([$NH_4OH$] to [TEOS]), the diameter of the Ag/$SiO_2$ nanocomposites obtained through reverse micelle synthesis is about 30±1.2 nm and the silver quantum dot is about 5±0.6 nm (with 95% confidence interval). The $SiO_2$ layer thickness would then be about 12 nm (FIG. 15B).

The formation step for agglomeration during the synthesis of the nanocomposites has not been identified. It is known, however, that nanocomposite particles trapped in the reverse micelle do not agglomerate because of the protective layer of surfactant, thus, washing out the surfactant layer is believed to induce agglomeration. Therefore, in order to synthesize unagglomerated nanocomposite particles, it is important and necessary to wash and disperse the nanocomposites simultaneously.

Dispersion and Morphology of Ag/$SiO_2$ Nanocomposite Particles Using HPLC

A size exclusion HPLC system was employed to simultaneously wash and disperse nanocomposite particles in order to produce well-dispersed Ag/$SiO_2$ suspensions. FIG. 16 shows the morphology of silica microspheres used as a stationary phase in the HPLC system. The silica particles were uniform spheres with a mean particle size of 20 μm and a pore size of 65 Å (surface area 425 $m^2/g$). A random packing density of 57% was obtained when the silica microspheres were dry-packed in the HPLC column. This generated a column porosity as high as 43%, which could form multiple micro-channels for nanocomposites to migrate during HPLC operation. The silica microspheres were treated with APS to produce positive charges, which prevented the positively charged Ag/$SiO_2$ nanocomposites from sticking on the surface of the stationary phase silica, a critical step in the HPLC protocol.

The spectrum shown in FIG. 17 reflects the washing process of Ag/$SiO_2$ inside the HPLC column. Elution of Ag/$SiO_2$ from the HPLC column took about 3 minutes when the extraction solvent (ethanol/water, volume ratio 7:3) was being pumped at 2 mL/min. The spectral intensity increased significantly at the onset point where Ag/$SiO_2$ nanocomposite particles passed through the detector, and a stable suspension was continuously collected at the HPLC terminal. The HPLC spectrum appeared to be a relatively narrow band with a high intensity (recorded as voltage because of the HPLC detection setup) accompanied by a secondary shoulder observed in the range of the washing cycles, which was the basis for collecting a well-washed Ag/$SiO_2$ suspension. Deconvolution of the spectrum by PEAKFIT® yielded three discrete peaks (area ratio of the three peaks was 1.1:1.8:1, and the central positions of the peaks were 95.1 s, 112,2 s and 150.7 s), which might correspond to the resolution of the HPLC column for individual Ag/$SiO_2$ nanocomposite particles and their aggregates (doublets, triplets, etc.). This suggested that the concentration of Ag/$SiO_2$ nanocomposite particles was very high based on the Beer-Lambert law.

The entire washing procedure took about 45 minutes, including an actual elute collection time of about 3 minutes. This is much more efficient than conventional washing procedures, such as centrifugation and sedimentation. The profile of the spectra suggested that the majority of the Ag/$SiO_2$ nanocomposite particles traveled through the HPLC column at a constant rate, which allowed the nanocomposite particles to continuously move inside the interstitial channels and thereby reduced the chance that the nanocomposites would aggregate and deposit on the surface of the stationary $SiO_2$ microspheres. The asymmetrical profile of the spectra, however, indicated that a small number of Ag/$SiO_2$ nanocomposite particles needed a longer time to go through the column due to the variation of particle size, as stated by the chromatography principle that smaller particles tend to take more time to elute compared to larger particles. This could indicate that a few doublet, triplet or even larger clusters were formed in the washing process, along with individual Ag/$SiO_2$ nanocomposite particles.

Figure 18:
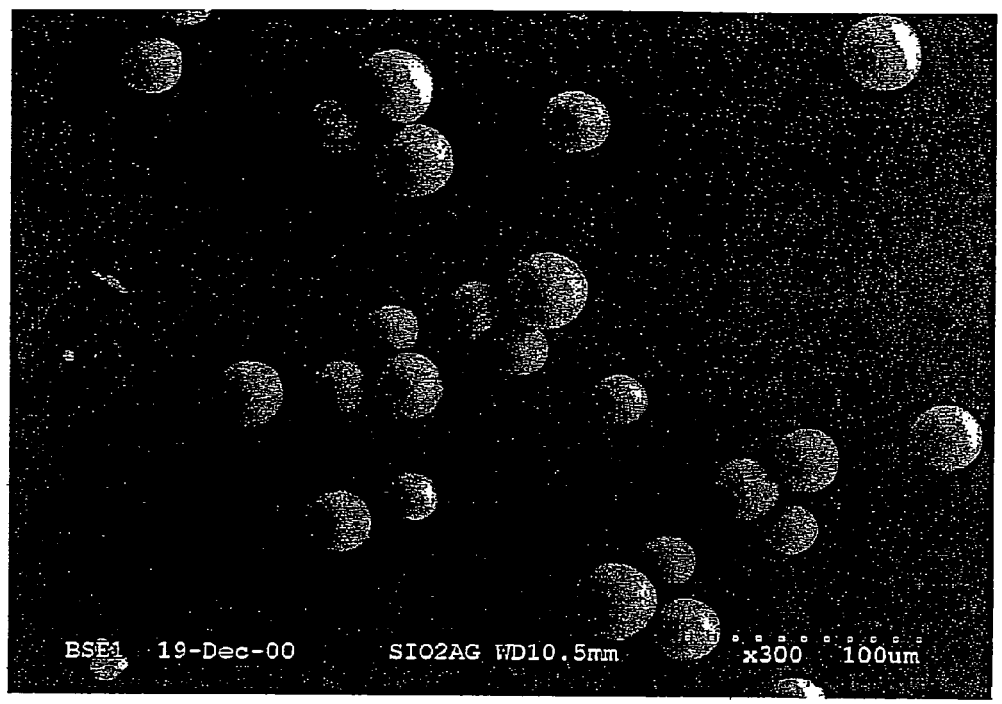
FIG. 18 shows an SEM image of $SiO_2$ microspheres used as the stationary phase in the HPLC system. The $SiO_2$ microspheres were treated with APS (90 g $SiO_2$ mixed with 0.336 mL APS, 1.5 mL glacial acetic acid, 7.5 mL DI water and 150 mL ethanol, stirred overnight and dried at 70° C.). The surface area is 425 $m^2/g$ with an average pore size of 6.5 nm.

FIG. 18A-B shows the morphology of Ag/$SiO_2$ nanocomposite particles washed by the HPLC method. FIG. 18A are two suspensions of Ag/$SiO_2$ nanocomposite particles. FIG. 18B are three digital images of the Ag/$SiO_2$ nanocomposite particles. According to the UV-vis analysis from 200 to 600 nm, the Ag/$SiO_2$ nanocomposite particles were free of surfactant within instrumental detection limits because the characteristic 280 nm absorption band for Igepal CO-520 was not identified. The zeta potential, +30 mV, strongly indicates robust surface grafting with APS even after the HPLC washing. The average size of the Ag/$SiO_2$ nanocomposite particles remained the same as was determined by TEM prior to the HPLC washing, with a Ag core of 5±0.6 nm and an overall diameter of about 30±1.2 nm (R=2, H=100, X=1). An average size of 20.3±1.5 nm was observed for R=8, H=300 and X=1 after HPLC washing. Along with individual nanocomposites, nanoscale clusters formed by two, three or four particles also were observed in HRTEM. Fortunately, aggregations with continuous inter-particle connections were not found. This implies that the HPLC method breaks the nanocomposite aggregation down to a size that allows the nanocomposites to penetrate through the interstitial channels.

Figure 19:
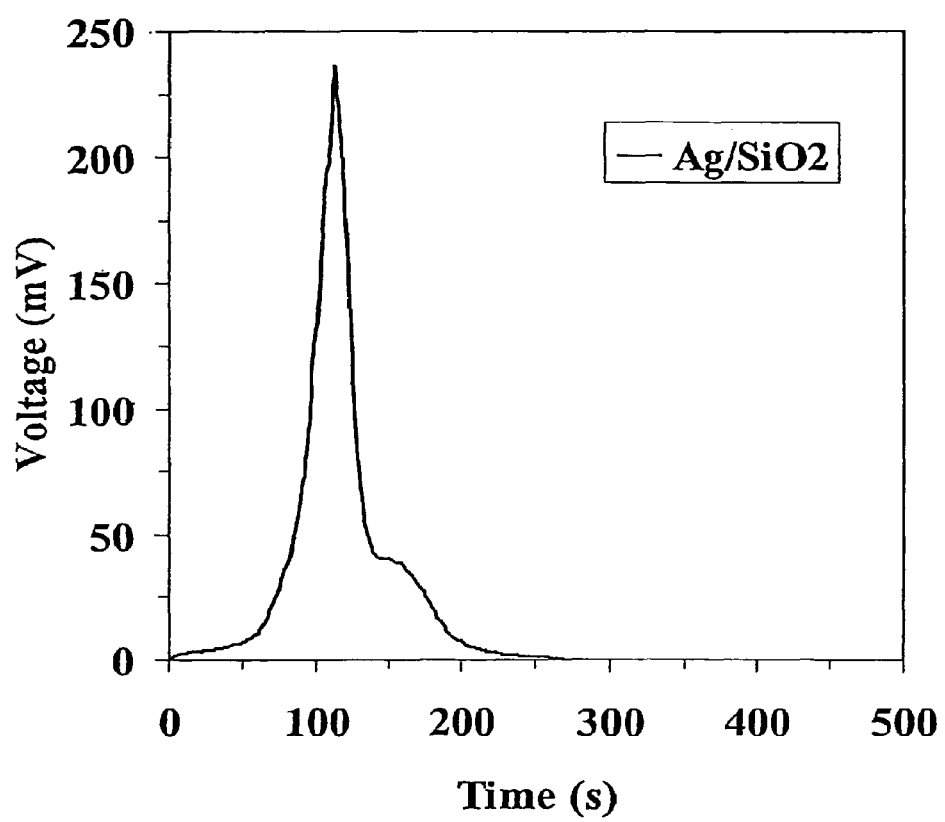
FIG. 19 is an HPLC spectrum of an Ag/$SiO_2$ ethanol/water suspension (R=2, H=100, X=1) washed with the HPLC system. Spectrum was acquired at 405 nm (surface plasmon resonance of Ag quantum dots) by UV-vis detector. The washing solvent is an ethanol/water solution (volume ratio 7:3), and the flow rate is 2 mL/min. The spectrum was deconvoluted by PEAKFIT®, the central positions of the peaks are 95.1, 112.2 and 150.7 s.

An AFM image of Ag/SiO$_2$ ethanol/water suspension (R=2, H=100, X=1) spin-coated onto a freshly cleaved mica substrate is shown in FIG. 19. At a spin rate of 1500 rpm, nanocomposite particles were sparsely distributed on the surface of the mica. Further analysis indicated that the mean particle size was around 60 nm, which derived an AAN of about 2 if the particle size of 30 nm in HRTEM is taken as the primary unit. Furthermore, the Ag/SiO$_2$ suspension treated with HPLC turned out to be very stable as confirmed experimentally by sedimentation tests over a span of one month.

The state of dispersion of the Ag/SiO$_2$ ethanol/water suspension was determined by a dynamic light scattering method. The hydrodynamic size distribution of the Ag/SiO$_2$ nanocomposite particles is shown in FIG. 20 (R=8, H=300, X=1). A collective average size of 18.6±1.5 nm was found for the Ag/SiO$_2$ nanocomposite particles with an extremely narrow monomode distribution. The light scattering result was in very good agreement with the particle size measured by TEM (20.3±1.5 nm). The AAN for the HPLC-washed sample was around 1.0. This implies that the Ag/SiO$_2$ nanocomposite particles were well dispersed in ethanol/water cosolvent after HPLC washing, because light scattering is more accurate for revealing the collective state of dispersion for colloidal suspensions. The consistency between the dynamic light scattering data and the TEM size analysis indicates that the hydrodynamic effect is compressed, which reflects the presence of a certain amount of ions in the as-prepared suspension.

APS Grafting

Silane coupling agents are frequently used to modify the surface of silica-based nanoparticles. Table I summarizes some of the silane coupling agents utilized for a number of applications. APS is one of the most commonly used silane coupling agents. The effectiveness of APS surface grafting is illustrated in FIG. 21. Ag/SiO$_2$ nanocomposite particles without an APS coating showed a weak negative charge when the pH is higher than pH 2 in an ethanol/water solution. The zeta potential curve became flat and a plateau was reached when the pH was above 7.0, with a peak value of about −30 mV. However, the APS-grafted Ag/SiO$_2$ nanocomposite particles gained a relatively high surface charge and converted from negative to positive. In the acidic region below pH 7.0, the APS-coated Ag/SiO$_2$ nanocomposite particles showed zeta potentials as high as 30 mV, and no significant APS concentration effect was observed. By contrast, the SiO$_2$ microspheres exhibited a noticeable increase of zeta potential when the APS concentration reached 1.5 w/o (FIG. 22). Most likely, this is due to the high surface area and porous nature of the SiO$_2$ microspheres. A detailed discussion of the graft mechanism has been described elsewhere (Plueddemann, E. P., "Silane coupling agent," pp 29-48, Plenum Press, NY, 1982; Ung, T. et al., Langmuir, 14:3740-3748, 1998; Chiang, C. H. et al., J. Colloid Interface Sci., 74(2):396-403, 1980; Chiang, C. H. et al., J. Colloid Interface Sci., 86(1):26-34, 1982). The main reaction has been described as follows:

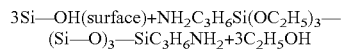
3Si—OH(surface)+NH$_2$C$_3$H$_6$Si(OC$_2$H$_5$)$_3$—
(Si—O)$_3$—SiC$_3$H$_6$NH$_2$+3C$_2$H$_5$OH This reaction implies that the silane groups on the surface of the Ag/SiO$_2$ nanocomposite particles were replaced by siloxane groups and ethanol was released as a consequence of the Si—O bond formation. This configuration was exclusively desired in which the amine group tail points to the solvent and protonates at pH <7.0. As a result, a positive charge is readily accomplished in an acidic pH range owing predominantly from the positively charged amine groups from the APS. The zeta potential measurements indicate that the surface charge for the treated samples was unanimously positive at pH <7.0. A further decrease in pH to below pH 6 would rapidly increase the zeta potential to a plateau value of around +30 mV, which supports the proposed theoretical interpretation.

Figure 23:
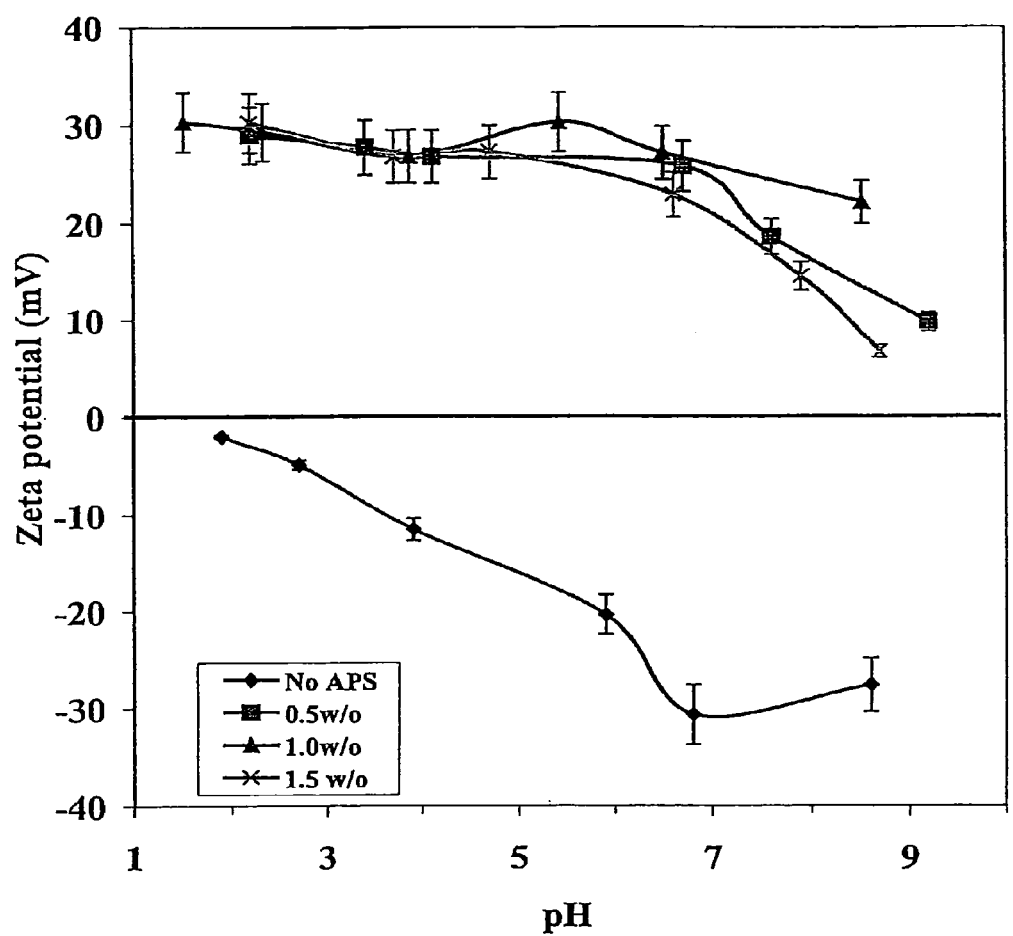
FIG. 23 illustrates the zeta potential of Ag/$SiO_2$ nanocomposite (R=2, H=100, X=1) ethanol/water suspensions as a function of pH and APS concentration. Noted is the conversion of negative to positive charge after the addition of APS. The pHs of the suspensions were measured using a Sentron pH meter calibrated against standard aqueous buffer solutions. Error bars are the 95% confidence interval.

The importance of surface grafting of both the Ag/SiO$_2$ nanocomposite particles and the SiO$_2$ microspheres with APS is shown in FIG. 15, which shows an AFM image of an untreated SiO$_2$ nanocomposite after the HPLC washing. The HPLC column was easily blocked in the washing process prior to surface grafting of Ag/SiO$_2$ with APS. This can be explained if the surface morphology shown in FIG. 23 is taken into account. A three-dimensional view of the silica microsphere indicated that the previously smooth surface was significantly compromised due to the interaction with the Ag/SiO$_2$ nanocomposite particles. The morphology of the silica microspheres prior to the HPLC washing was uniformly spherical with a very low surface roughness according to SEM (FIG. 16) and AFM observations. However, the surface was compromised during HPLC washing and agglomerations of Ag/SiO$_2$ nanocomposite particles were attached onto the surface of the large silica micropheres. One of the aggregates that was stuck on the silica microsphere was about 0.5 μm across, thus consisting of at least 150 individual nanocomposite particles, if the primary particle size is about 30 nm. Although the exact mechanism for the aggregation of Ag/SiO$_2$ nanocomposite particles onto the surface of the SiO$_2$ microspheres is not well understood, the columbic interaction between APS-grafted Ag/SiO$_2$ nanocomposite particles and negatively charged spherical SiO$_2$ microspheres plays a significant role in the evolution of agglomeration. As the HPLC washing proceeds in the weak acidic pH range (pH 5.0~7.0), the nanocomposites gain a positive charge because of the APS coating, while the SiO$_2$ microspheres are negatively charged in this pH range. When the two oppositely charged nanocomposites approach each other, the tendency of aggregation is enhanced due to the electrostatic attraction. This probably is the mechanism that causes the HPLC column to block, thus causing the initial washing and collection attempts to fail. Therefore, the same surface grafting was applied to the SiO$_2$ microspheres as was applied to the Ag/SiO$_2$ nanocomposite particles, in order to control the surface potential and thereby eliminate nanocomposite agglomeration. This protocol proved to be the critical step in the HPLC washing of the Ag/SiO$_2$ nanocomposite particles based on size exclusion chromatography. Stable suspensions of Ag/SiO$_2$ nanocomposite particles in ethanol/water solvent were routinely synthesized when this protocol was followed precisely. Prior methods for synthesizing nanocomposite particles, such as those employed by Tan, W. et al. described above, do not use the key features of silane coupling agents, dilution of the nanocomposites in an ethanl/water solution, and a size exclusion HPLC or sedimentation and filtration system.

Washing Solvent

Along with the surface modification of the nanocomposite particles with dispersing agent for both the mobile and the stationary phase, the selection of a proper extraction solvent also is important for successful operation of the HPLC washing protocol. It has been found that selection of the washing solution is important to prevent agglomeration. For example, the Ag/SiO$_2$ nanocomposite particles remain clustered in the upper part of the HPLC column when DI water, pure anhydrous ethanol, isopropanol and acetone solvents were used. When the preferred ethanl/water co-solvent (ethanol:water= 7:3 vol) was pumped in, the clusters started to migrate downward and eventually eluted out of the column as well dispersed nanoparticles.

Suspension pH

Figure 24:
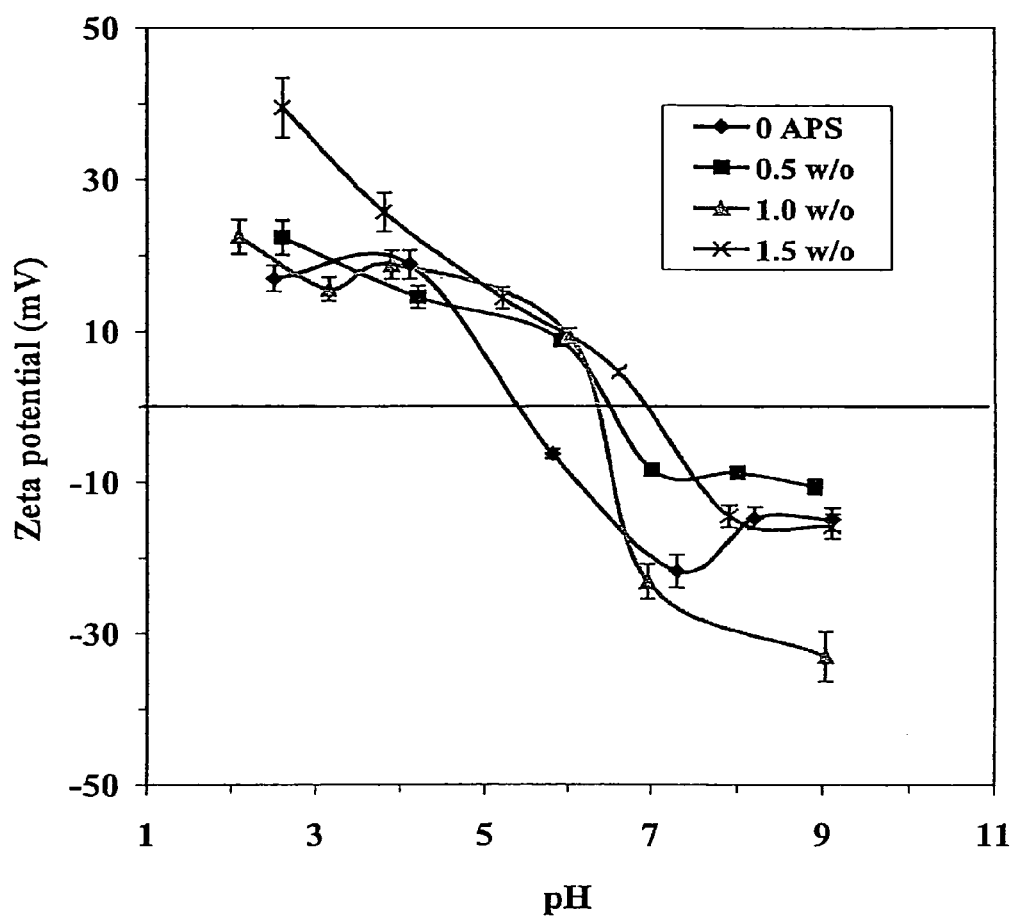
FIG. 24 illustrates the zeta potential of $SiO_2$ microspheres as a function of pH and APS concentration. The average size of $SiO_2$ is 20 μm with a surface area of 425 $m^2/g$ and a 6.5 nm average pore size. The $SiO_2$ microspheres were dispersed in ethanol/water (7:3 vol) solution. The pHs of the suspensions were measured using a Sentron pH meter calibrated against standard aqueous buffer solutions. Error bars are the 95% confidence interval.
Figure 25:
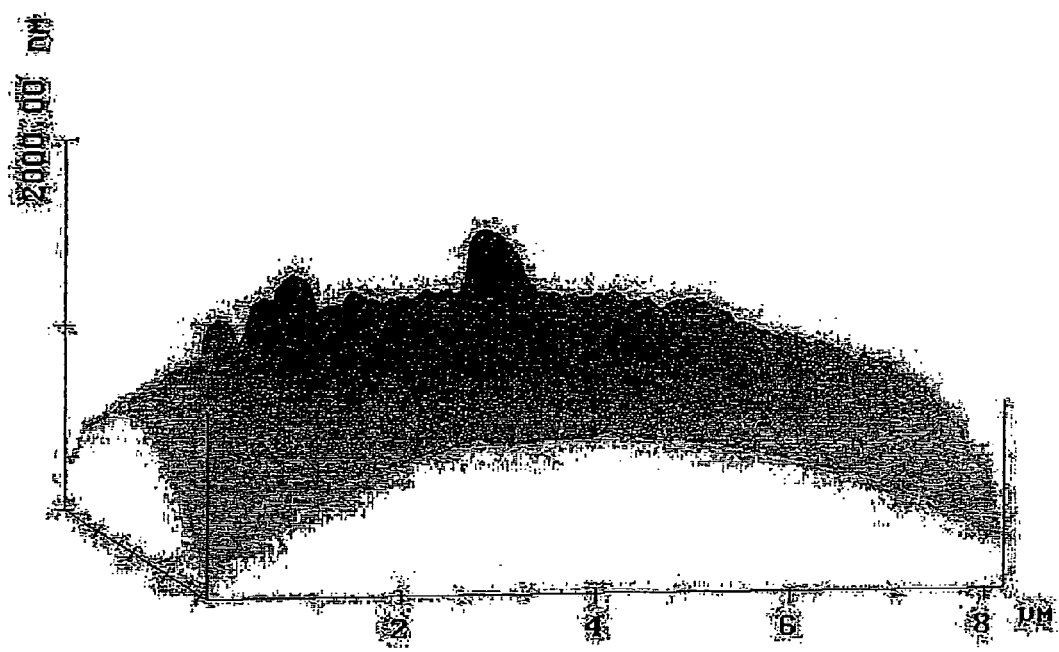
FIG. 25 shows an AFM image of a Ag/$SiO_2$ nanocomposite (R=2, H=100, X=1) aggregation formed on the surface of a $SiO_2$ microsphere. APS surface coating only was applied to the Ag/SiO$_2$ nanocomposites (average size 30 nm), and the SiO$_2$ microspheres were used without further treatment (average size 20 μm). SiO$_2$ microspheres from a blocked HPLC column were placed on a freshly cleaved mica substrate.

Control over suspension pH is an important parameter when making well-dispersed nanocomposite particle dispersions. FIG. 24A shows the particle size distribution by dynamic light scattering. As shown in FIG. 24B, at a pH of 2.8, the Ag/SiO$_2$ nanocomposite suspension had considerable agglomeration based on the TEM and dynamic light scattering analysis, and the AAN was about 15 due to the bimodal particle size distribution. In the alkaline range with a measured pH of 9.7, the dissolution of the SiO$_2$ shell leads to the formation of a Ag metal core contact and a small particle size. The poorly dispersed suspension had an AAN of 0.02, which indicates damage to the nanocomposite architecture. A well-dispersed Ag/SiO$_2$ nanocomposite suspension with an AAN of about 1 was obtained when the pH is adjusted to around pH 6.0. Dynamic light scattering data of this sample suggests that the particle size distribution is monomodal, which is consistent with the TEM analysis. The corresponding AAN was around 1, indicating a well-dispersed suspension at a pH of about 6.0.

Column Length

Another parameter that affects the efficiency of the HPLC washing is the size of the HPLC column. More washing solvent and time are required for a large dimension column. Three types of HPLC columns having different specific size dimensions were studied. Columns HR 16 (16×500 mm) and HR 10/10 (10×100 mm) were too long for the Ag/SiO$_2$ nanocomposite particles to elute, whereas the short column HR 5/5 (5×50 mm) proved to be suitable for Ag/SiO$_2$ nanocomposite dispersion. The total accessible pore volume (V) to nanocomposite with size R$_0$ is expressed as follows:

$$V = \pi \cdot (R_p - R_0)^2 \times (L - R_0)$$

where R$_p$ is the pore radius, and L is the column length. For Ag/SiO$_2$ nanocomposite particles, the condition L>>R$_0$ is satisfied and the total volume V is proportional to L. Hence, a larger column length L definitely increases the washing time.

3. Conclusions

The silane coupling agent, APS, effectively reacted with the Ag/SiO$_2$ nanocomposite particles, thereby increasing the surface charge of the Ag/SiO$_2$ nanocomposite particles to ensure that the Ag/SiO$_2$ nanocomposite particles could diffuse through the positively charged spherical SiO$_2$ stationary phase matrix during HPLC operation. Size exclusion chromatography based on this principle eliminated agglomeration and deposition of Ag/SiO$_2$ nanocomposite particles on the silica microspheres. Thus, elute dispersion generated by this HPLC method demonstrated excellent homogeneity and stability with a zeta potential up to +30 mV. The resulting ethanol/water suspension is an ideal precursor for colloid chemistry-based "bottom-up" nanoscale assembly for macroscopic devices. Processing parameters, such as surface modification of both mobile and stationary phases, solvent, suspension pH and column dimension, are of great importance to the HPLC dispersion protocol. In the separation process, this approach could be extended to many similar nanoparticulate systems where surfactant-free dispersion is a major concern.

EXAMPLE 2

Rhodamine B/SiO$_2$ Nanocomposite Particle, AAN=1

To perform the nanocomposite particle syntheses using a water-in-oil synthesis method, polyoxyethylene(5)nonphenyl ether (Igepal® CO-520), cyclohexane, tetraethoxysilane (TEOS), 3-aminopropyltrimethoxysilane (APS), ammonium hydroxide, and acetic acid were purchased from Aldrich Chemical Co. (Milwaukee, Wisc.). Each of the chemicals utilized in the microemulsion synthesis process were used as received. The aqueous stock solutions used were prepared with deionized (DI) water (specific conductivity=0.4×10$^{-7}$ S/m). A variety of organic fluorophore dyes can be encapsulated in the nanocomposite particles including the sodium salt of fluorescein, Rhodamine 123, Rhodamine B, Indocyanine Green, (Aldrich Chemical Co., Milwaukee, Wisc.), Rhodamine WT (Presto Dye Chem Co., Philadelphia, Pa.), cascade blue acetyl azide (Molecular Probes, Inc. Eugene, Oreg.), Cy 3 amidite, and Cy 5 amidite (Amersham Biosciences, Piscataway, N.J.).

To form a reverse micelle microemulsion, 4 mL Igepal® CO-520, 10 mL cyclohexane and 0.325 mL 10$^{-2}$ M Rhodamine B solution were combined in a sealed falcon cup at room temperature. The solution then underwent stirring at moderate speed for 30 minutes. Next, 0.05 mL NH$_4$OH was added and the suspension was stirred for 15 minutes. Subsequently, 0.08 mL TEOS was added. The micelles were allowed to mature for approximately 24 hours, followed by the addition of 0.013 mL of the silane coupling agent APS. The microemulsion was broken while rapidly stirring with 50 mL of 0.02 M acetic acid/ethanol solution.

The state of dispersion of the nanocomposite Rhodamine B/SiO$_2$ suspension was analyzed using the average agglomeration number (AAN) approach. The sample parameters were R=4, H=100, X=1. QELS characterization provided a particle size of D$_{50}$=32.0 nm and a standard deviation=6.9 nm with 95% confidence interval. Characterization by TEM gave a particle size of 25 nm±5 nm (30 particles were counted). The AAN for the Rhodamine B/SiO2 nanosuspension was 1. Thus, the suspension can be classified as well-dispersed. FIG. 27A-B shows TEM images of organic core/silica shell nanocomposite particles in which the organic core material is rhodamine B at two different magnifications.

EXAMPLE 3

Synthesis of Calcium Phosphate Nanocomposite Particles

The synthesis of calcium phosphate shell nanocomposite particles includes the preparation of two separate microemulsions. The nonionic surfactant, poly(oxyethylene) nonylphenyl ether (Igepal® CO-520, Aldrich Chemical Co.), cyclohexane (Aldrich Chemical Co.) and distilled water serve as the basis of the microemulsions. The surfactant was used without further purification. The size of the resulting nanoparticles was controlled by varying the ratio of water to surfactant (R=[water]/[surfactant]. Calcium chloride dehydrate (CaCl$_2$, 99+%, Aldrich Chemical Co.) and sodium hydrogenphosphate (Na$_2$HPO$_4$, 99+%, Aldrich Chemical Co.) serve as the precursors for the calcium phosphate shell. Sodium metasilicate (SiO$_2$, 44-47%), tetraethoxysilane (TEOS, 99%), and ammonium hydroxide (NH$_4$OH) (29%) (all from Fisher Scientific) were used as received.

Two microemulsions each of 10 mL total volume, consisting of 2 mL Igepal, 5 mL cyclohexane and deionized water, containing therapeutic agent/drug/organic fluorescent material or deionized water containing sodium metasilicate, respectively, were prepared at ambient temperature. The microemulsions were rapidly mixed. Once the solutions were uniform in appearance, the precursor materials were added and stored for approximately 15 minutes. The microemulsions were then slowly and continuously combined using a separatory funnel. A dispersant in the form of a silane coupling agent or a citrate solution was added to the suspension to modify particle surface charge. The microemulsion was broken using an acid/alcohol solution and washed and dispersed using HPLC. Calcium phosphate silicate nanocomposite particles can be synthesized through the combination of Examples 2 and 3. First, as described in Example 2, a core-$SiO_2$ shell nanocomposite particle can be synthesized in a manner such that the shell is 1-3 nm thick. Then, the particles can be integrated into one of the precursor microemulsions present in Example 3 and treated accordingly.

EXAMPLE 4

Rhodamine WT/$Ca_{10}(PO_4)_2(OH)_2$ Nanocomposite Particle, AAN=1

All materials were received and prepared as described in Example 2.

Two separate microemulsions, each containing Igepal® CO-520, cyclohexane and aqueous precursor solutions were prepared by rapidly mixing the components in a sealed falcon cup at ambient temperature. Microemulsion #1 consisted of 4 mL Igepal® CO-520, 10 mL cyclohexane, 1.2 mL $10^{-2}$ M calcium chloride solution, and 1 mL $10^{-3}$ M Rhodamine WT solution. Microemulsion #2 consisted of 4 mL Igepal® CO-520, 10 mL cyclohexane, 1.2 mL $6×10^{-3}$ M sodium dihydrogenphosphate solution, and 500 ppm sodium metasilicate in 1 mL DI $H_2O$. Both of the microemulsions were allowed to mix for five minutes. Microemulsion #2 then was slowly added drop wise to Microemulsion #1 using a disposable plastic pipette. The micelles were allowed to age for two minutes. The silane coupling agent, trimethoxysilylpropyl-diethylenetriamine (DETA) was added to the suspension to modify nanoparticle surface charge. The microemulsion then was immediately broken while rapidly stirring with 50 mL of 0.02 M acetic acid/ethanol solution.

The state of dispersion of a nanocomposite Rhodamine WT/Ca10(PO4)6(OH)2 suspension was analyzed using the average agglomeration number (AAN) approach. The sample parameters were R=11, H=100, X=1. QELS characterization provided a particle size of $D_{50}$=67.0 nm. Characterization by TEM gave a particle size of 60 nm±10 nm. The AAN for the Rhodamine WT/Ca10(PO4)6(OH)2 nanosuspension was 1. Thus, the suspension can be classified as well-dispersed.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

The invention claimed is:

1. A method of preparing unagglomerated, dispersed core/shell nanocomposite particles in suspension, comprising:
   preparing a reverse micelle microemulsion by forming a mixture comprised of a surfactant, a solvent and an aqueous core precursor at room temperature; adding a shell precursor material;
   treating the reverse micelle microemulsion with a dispersing agent;
   breaking the microemulsion to form a suspension of nanocomposite particles by adding a breaking agent to the microemulsion; and
   washing and dispersing the suspension of nanocomposite particles simultaneously to produce said unagglomerated, dispersed core/shell nanoparticles in suspension.

2. The method of claim 1, wherein the acid/alcohol solution maintains the suspension of nanocomposite particles at a pH of between about 5 and 9 and further wherein the breaking agent is an acidified alcohol solution.

3. The method of claim 1, wherein the breaking agent is an acetic acid/ethanol solution and wherein the dispersing agent is selected from the group consisting of citrate, oxalate, succinate and phosphonates.

4. The method of claim 1, further comprising the additional steps of:
   stirring the mixture for about 2 minutes to 24 hours;
   adding base to form a suspension;
   stirring the suspension for about 2 minutes to 24 hours;
   wherein the shell percursor material is a silica or titania material; and
   maturing the microemulsion for about 24 hours, wherein said unagglomerated dispersed core/shell nanoparticles in suspension maintain the nanostructure throuuh said silica or shell precursor material additions.

5. The method of claim 4, wherein the surfactant is poly (oxyetheylene)nonylphenyl ether.

6. The method of claim 4, wherein the solvent is cyclohexane.

7. The method of claim 4, wherein the aqueous core precursor is selected from the group consisting of Au, Ag, Co, Ni, Cu, CdS; Pt, organic pigments, organic dyes, organic fluorophores such as the sodium salt of fluorescein, rhodamine, rhodamine derivatives, fluorescein, fluorescein derivatives, luciferin and one or more drug agents.

8. The method of claim 7, wherein the drug agent is a genetic therapeutic agent which delivers nucleic acids to cells in a transcriptionally active form.

9. The method of claim 7, wherein the fluorescein and fluorescein derivatives are selected from the group consisting of BDCECF; BCECF-AM; Calcien-AM; 5,(6)-carboxy-2', 7'-dichlorofuorescein; 5,(6)-carboxy-2 '7'-dichlorofuorescein diacetate Nsuccinimidylester; 5,(6)-carboxyeosin; 5,(6)-carboxycosin diacetate; 5,(6)-carboxyfluorescein; 5-carboxyfluorescein; 6-carboxyfluorescein; 5,(6)-carboxyfluoresceinacetate; 5,(6)-carboxyfluorescein acetate N-succinimidyl ester; 5,(6)-carboxyfluorescein Nsuccinimidylester; 5(6)-carboxyfluorescein octadecyl ester; 5,(6)-carboxynaphthofluoresceindiacetate; eosin-5-isothiocyanate; eosin-5-isothiocyanate diacetate; fluorescein-5(6)-carboxamidocaproic acid; fluorescein-5(6)-carboxamidocaproic acid N-succinimidyl ester; fluorescein isothiocyanate; fluorescein isothiocyanate isomer 1; fluorescein isothiocyanate isomer 2; fluorescein isothocyanate diacetate; fluorescein octadecyl ester; fluorescein sodium salt; napthofluorescein; napthofluorescein diacetate; or N-octadecyl-N7-(5 fluoresceinyl) thiourea (F18).

10. The method of claim 7, wherein the rhodamine and rhodamine derivatives are selected from the group consisting of 5,(6)carboxytetramethylrhodamine; 5-carboxytetramethylrhodamine N-succinimidyl ester; 6-carboxytetramethylrhodamine Nsuccinimidylester; 5,(6)-carboxytetramethylrhodamine N-succinimidyl ester; 5,(6)-carboxy-X-rhodamine; dihydrorhodamine 123; dihydrorhodamine 6G; lissaninc rhodamine; rhodamine 110 chloride; rhodamine 123, rhodamine B hydrazide; rhodamine,B; and rhodamine WT.

11. The method of claim 7, wherein the organic pigments and dyes are selected from the group consisting of hematoporphyrin dyes, such as 7,12-bis(1-hydroxyethyl)-3,8,13,17-tetramethyl-2 1 H,23H-porphine-2 and 18-dipropanoic acid, and cyanine dyes and derivatives, such as indocyanine green; indoine blue; R-phycoerythnn (PE), PE-Cy 5; PE-Cy 5.5;

PE-Texas Red; PE-Cy 7; Cy 3 NHS ester; Cy 3 maleimide and hydrazide; Cy 3B NHS ester; Cy 3.5 NHS ester; Cy 3 amidite; Cy 5 NHS ester; Cy-5; Cy 5 amidite; Cy 5.5; Cy-5.5 NHS ester; Cy 5.5 annex in V; Cy 7; Cy 7 NHS ester; Cy 7Q NHS ester; allophycocyanin (APC); APC-Cy 7; APC Cy 5.5; propidium iodide (PI); crystal violet lactone; patent blue VP; brilliant blue G; or cascade blue acetyl azide.

12. The method of claim 1, wherein the shell precursor material is selected from the group consisting of $SiO_2$, $TiO_2$, ZnO, $Fe_2O_3$, $Zr_2$, NiO and $GeO_2$, Sn, Pb, Ag and Au, $CaPO_x$, $CaCO_3$, tetraethoxysilane (TEOS), titanium (IV) isopropoxide, and a calcium phosphosilicate having the general formula $Ca_x(PO_4)_y(OH)_z(SiO_2)_a$.

13. The method of claim 12, wherein the precursor is tetraethoxysilane (TEOS).

14. The method of claim 12, wherein the precursor is titanium (IV) isopropoxide (TIPO).

15. The method of claim 1, wherein the dispersing agent is a silane coupling agent is selected from the group consisting of 3-aminopropyltrimethoxysilane, 3-aminopropylsilsesquioxane, 3-glycidoxypropyltrimethoxysilane, trimethoxysilylpropyldiethylenetriamine, 3-trimethoxysilylpropylsuccinic anhydride and amide-linked carboxyl groups.

16. The method of claim 15, wherein the silane coupling agent is 3-aminopropyltrimethoxysilane.

17. The method of claim 1, wherein the core of the nanocomposite particle contains hydrogel materials selected from the group consisting of polyvinyl alcohol, polymethyl methacrylate and 2-hydroxylethyl methacrylate.

18. The method of claim 1, further comprising adding a surface modifier to said dispersing agent in order to use the nanocomposite particles in vivo in an animal or human.

19. The method of claim 18, further wherein said surface modifier is a binder.

20. The method of claim 19, wherein the binders are antibodies.

21. The method of claim 4, further comprising attaching moieties selected from the group consisting of organic groups, metals, enzymes, macromolecules and plasmids to the shell precursor material.

22. The method of claim 4, wherein the diameter of the nanocomposite particles is modified by manipulating the molar ratio of aqueous phase to surfactant, the molar ratio of aqueous phase to the shell precursor material, and the molar ratio of base to the shell precursor material.

23. The method of claim 1, further comprising:
using a size-exclusion HPLC system to wash and disperse the nanocomposite articles comprised of an HPLC column packed with spherical silica beads of about I µm to about 100 µm in diameter;
pumping breaking agent through the HPLC column;
limping the nanoparticle suspension into the HPLC column through a stationary phase at a flow rate from of about 1 ml/min to about 100 ml/min;
measuring changes in UV absorbance or fluorescence with detectors connected to an out-flow of the HPLC packed column in order to determine when the column is fully saturated with nanoparticles; and
eluting and redispersing the nanoparticles with a water miscible organic solvent and water solution of up to about 250 volume percent solution.

24. The method of claim 23, wherein the spherical silica beads are about 20 µm in diameter.

25. The method of claim 23, wherein the water miscible organic solvent and water solution is up to about 70 volume percent solution.

26. The method of claim 23, wherein the HPLC column is about 5×50 mm in length.

27. The method of claim 23, wherein the stationary phase is comprised of microspheres which have been treated with the dispersing agent.

28. The method of claim 1, wherein the nanocomposite particles have a primary particle size of between about 1 to 100 nm in diameter.

29. The method of claim 1, wherein the nanocomposite particles have a primary particle size of between about 10 to 20 nm in diameter.

30. The method of claim 1, wherein the nanocomposite particles have a primary particle size of about 20 nm in diameter.

31. A method of synthesizing unagglomerated, dispersed core/shell nanocomposite particles, comprising:
preparing a reverse micelle microemulsion, comprising:
(i) forming a mixture comprised of poly(oxyetheylene)-nonylphenyl ether, cyclohexane and an aqueous active-medical-agent precursor at room temperature;
(ii) stirring the mixture for about 30 minutes;
(iii) adding $NH_4OH$ to form a suspension;
(iv) stirring the suspension for about 15 minutes;
(v) adding a shell precursor; and
(vi) maturing the microemulsion for about 24 hours;
treating the reverse micelle microemulsion with 3-aminopropyltrimethoxysilane;
breaking the microemulsion to form a suspension of the nanocomposite particles by adding to the micro emulsion an acetic acidethanol solution which maintains the suspension at a pH of between about 6 and 7; and
washing and dispersing the suspension of nanocomposite particles using a size-exclusion HPLC system comprising:
(i) packing a HPLC column with spherical silica beads of about 20 µm in diameter;
(ii) pumping ethanol through the HPLC column;
(iii) pumping the nanoparticle suspension into the HPLC column through a stationary phase at a flow rate of about 1 ml/min;
(iv) measuring changes in UV absorbance or fluorescence with detectors connected to an out-flow of the HPLC packed column in order to determine when the column is fully saturated with nanoparticles; and
(v) eluting and redispersing the nanoparticles with an ethanol/water solution of up to about 70 v/o water.

32. The method.of claim 1 further comprising the additional steps of forming a first mixture containing a surfactant, a solvent, a quantity of aqueous core precursors pH adjusted to pH 6-8, and calcium in the form of $Ca^{++}$; forming a second mixture containing a surfactant, a solvent, a quantity of aqueous core precursors pH adjusted to pH 6-8, and phosphorus in the form of $PO_4^{---}$ and optional $SiO_3^{--}$; and mixing together and maturing said first mixture and said second mixture for about 2 minutes.

33. The method of claim 32 wherein the aqueous core precursors are pH adjusted to pH 7.4.

34. The method of claim 32 wherein the surfactant is poly(oxyethyl ene) nonyiphenyl ether.

35. The method of claim 32 wherein the solvent is cyclohexane.

36. The method of claim 32 wherein the aqueous core precursor is selected from the group consisting of Au, Ag, Co, Ni, Cu, CdS; Pt, organic pigments, organic dyes, organic fluorophores such as sodium salt of fluorescein, rhodamine, rhodamine derivatives, fluorescein, fluorescein derivatives, luciferin and one or more drug agents.

37. The method of claim 36 wherein the drug agent is a genetic therapeutic agent which delivers nucleic acids to cells in a transcriptionally active form.

38. The method of claim 32 wherein the diameter of the nanocomposite particles is modified by manipulating the molar ratio of aqueous phase to surfactant, the molar ratio of aqueous phase to the shell precursor material, and the molar ratio of base to the shell precursor material.

39. A method of synthesizing unagglomerated, dispersed core\shell nanocomposite particles, comprising:
   preparing a reverse micelle microemulsion, comprising:
      (i) forming a first mixture comprised of poly(oxyetheylene)-nonylphenyl ether, cyclohexane, a drug agent precursor and $Ca^{++}$ at room temperature;
      (ii) forming a second mixture comprised of poly(oxyetheylene)-nonylphenyl ether, cyclohexane, a drug agent precursor and $PO4^{---}$ with optional $SO_2^-$; and
      (iii) mixing and maturing the first and second mixtures for about two minutes;
         treating the reverse micelle microemulsion with 3-aminopropyltrimethoxysilane;
   breaking the micro emulsion to form a suspension of the nanocomposite particles by adding to the microemulsion an acetic acid/ethanol solution which maintains the suspension at a pH of between about 6 and 7; and
   washing and dispersing the suspension of nanocomposite particles using a size-exclusion HPLC system comprising:
      (i) packing a HPLC column with spherical silica beads of about 20 μm in diameter;
      (ii) pumping ethanol through the HPLC column;
      (iii) pumping the nanoparticle suspension into the HPLC column through a stationary phase at a flow rate of about 1 ml/min;
      (iv) measuring changes in UV absorbance or fluorescence with detectors connected to an out-flow of the HPLC packed column in order to determine when the column is fully saturated with nanoparticles; and
      (v) eluting and redispersing the nanoparticles with an ethanov\water solution of up to about 70 v/o water.

40. The method of claim 4, wherein the shell precursor material is selected from the group consisting of $SiO_2$, $TiO_2$, ZnO, $Fe_2O_3$, $Zr_2$, NiO and $GeO_2$, Sn, Pb, Ag and Au, $CaPO_x$, $CaCO_3$, tetraethoxysilane (TEOS), titanium (IV) isopropoxide, and a calcium phosphosilicate having the general formula $Ca_x(PO_4)_y(OH)z(SiO_2)_a$, and wherein the reverse micelle microemulsion is synthesized by the addition of the first and second microemulsions to one another.

41. The method of claim 40, wherein the precursor is tetraethoxysilane (TEOS).

42. The method of claim 40, wherein the precursor is titanium (IV) isopropoxide (TIPO).

* * * * *